US009227901B2

(12) United States Patent
Ku et al.

(10) Patent No.: US 9,227,901 B2
(45) Date of Patent: Jan. 5, 2016

(54) PROCESS FOR PREPARING BICYCLIC AMINE DERIVATIVES

(71) Applicant: AbbVie Inc., North Chicago, IL (US)

(72) Inventors: Yi-Yin Ku, North Chicago, IL (US); Steven Hannick, North Chicago, IL (US); Ashok K. Gupta, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/933,961

(22) Filed: Jul. 2, 2013

(65) Prior Publication Data

US 2014/0012015 A1 Jan. 9, 2014

Related U.S. Application Data

(60) Provisional application No. 61/668,220, filed on Jul. 5, 2012.

(51) Int. Cl.
| | |
|---|---|
| C07C 233/23 | (2006.01) |
| C07C 49/755 | (2006.01) |
| C07C 49/697 | (2006.01) |
| C07C 233/59 | (2006.01) |
| C07C 233/60 | (2006.01) |
| C07C 231/12 | (2006.01) |
| C07D 207/24 | (2006.01) |
| C07C 231/14 | (2006.01) |
| C07C 233/14 | (2006.01) |
| C07D 207/38 | (2006.01) |
| C07C 233/06 | (2006.01) |

(52) U.S. Cl.
CPC ............ C07C 49/755 (2013.01); C07C 49/697 (2013.01); C07C 231/12 (2013.01); C07C 231/14 (2013.01); C07C 233/06 (2013.01); C07C 233/14 (2013.01); C07C 233/23 (2013.01); C07C 233/59 (2013.01); C07C 233/60 (2013.01); C07D 207/24 (2013.01); C07D 207/38 (2013.01)

(58) Field of Classification Search
CPC .................................................. C07C 233/23
See application file for complete search history.

(56) References Cited

U.S. PATENT DOCUMENTS

| 5,451,684 A | 9/1995 | McGarrity |
| 6,140,354 A | 10/2000 | Dax et al. |
| 2011/0112318 A1 | 5/2011 | Rivas-nass |

FOREIGN PATENT DOCUMENTS

| EP | 0624587 | 5/1994 |
| EP | 2107065 | 4/2008 |
| WO | 00/20376 | 4/2000 |
| WO | 2006/017045 | 2/2006 |
| WO | 2006/067412 | 6/2006 |
| WO | WO2006/060225 | * 6/2006 | ............ C07D 487/04 |
| WO | WO2006/081151 | * 8/2006 | ............ C07C 227/32 |
| WO | 2006/117369 | 11/2006 |
| WO | 2008/031749 | 3/2008 |
| WO | 2008093227 A1 | 8/2008 |

(Continued)

OTHER PUBLICATIONS

Meeuwissen et al. (Chem. Eur. J. 2009, 15, p. 10272-10279).*

(Continued)

*Primary Examiner* — Robert Havlin
(74) *Attorney, Agent, or Firm* — Lisa V. Mueller; Michael Best & Friedrich LLP

(57) ABSTRACT

The present invention provides a process for preparing a bicyclic amine derivative of the formula (Ia) or (Ib),

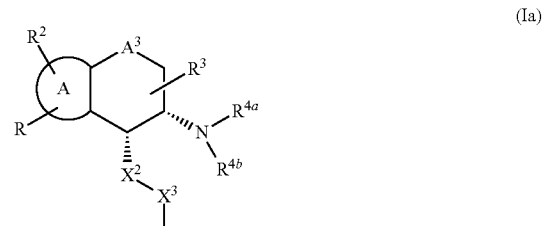

comprising the rhodium-catalyzed asymmetric hydrogenation of an enamine of the formula (II),

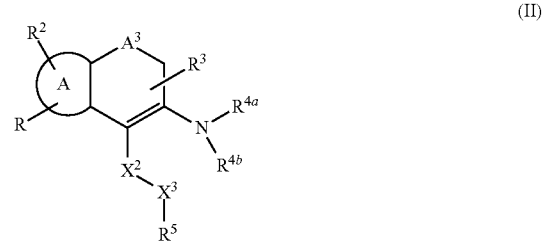

in the presence of a chiral ligand, wherein the chiral ligand is a chiral phosphine ligand.

9 Claims, No Drawings

(56) References Cited

FOREIGN PATENT DOCUMENTS

| WO | 2010/092180 | 8/2010 |
|---|---|---|
| WO | 2012/020131 | 2/2012 |

OTHER PUBLICATIONS

Arora P.K., et al., "Antifertility Agents: Part XLIV. Syntheis of 3-amino-4-phenylchromans," Indian Journal of Chemistry, 1985, vol. 24, pp. 845-857.

Dupau P., et al., "Enantioselective Hydrogenation of the Tetrasubstituted C=C Bond of Enamides Catalyzed by a Ruthenium Catalyst Generated in Situ," Advanced Synthesis & Catalysis, 2001, vol. 343 (4), pp. 331-334.

International Search Report and Written Opinion for Application No. PCT/US2013/049244, mailed on Oct. 9, 2013, 17 pages.

Meeuwissen J., et al., "Rhodium-P,O-bidentate Coordinated Ureaphosphine Ligands for Asymmetric Hydrogenation Reactions.," Dalton Transactions, 2010, vol. 39 (8), pp. 1929-1931.

Patureau F.W., et al., "Sulfonamido-phosphoramidite Ligands in Cooperative Dinuclear Hydrogenation Catalysis.," Journal of the American Chemical Society, 2009, vol. 131 (19), pp. 6683-6685.

Savel'Ev, et al., "Synthesis of 1 H-(1)benzothiopyrano(3,4-d)imidazol-4-ones," Chemistry of Heterocyclic Compounds, 1980, vol. 16 (4), pp. 363-367.

Soussi M., et al., "Palladium-cazalyted Coupling of 3-halosubstituted Coumarins,Chromenes, and Quinolones with Various Nitrogen-containing Nucleophiles," European Journal of Organic Chemistry, 2011, vol. 26, pp. 5077-5088.

Youngman M.A., et al., "The synthesis of Novel cis-alpha-substituted-betaaminotetralins," Synthetic Communications, 2003, vol. 33 (13), pp. 2215-2227.

Blaser, H-U. et al., "Solvias Josiphos ligands: from discovery to technical applications," Topics in Catalysis (2002) 19:3-6.

Doherty, S. et al., "Rhodium complexes of (R)-Me-CATPHOS and (R)-(S)-JOSIPHOS: highly enantioselective catalysts for the asymmetric hydrogenation of (E)- and (Z)-beta-aryl-beta-(enamido)phosphonates," Tetrahedron Asymmetry (2009) 20:1437-1444.

Lucarini, S. et al., "Diastereo- and enantioselective hydrogenation of a challenging enamide derived from 4-phenyl-2-tetralone: an appealing shortcut towards enantiopure cis-2-aminotetraline derivatives," Chem. Asian J. (2010) 5:550-554.

Ma, M. et al., "Rhodium-catalyzed asymmetric hydrogenation of beta-acetylamino acrylonitriles," Tetra. Asymmetry (2011) 22:506-511.

Molinaro, C. et al., "A practical synthesis of renin inhibitor MK-1597 (ACT-178882) via catalytic enantioselective hydrogenation and epimerization of piperidine intermediate," J. Org. Chem. (2011) epub ahead of print.

Pryde, D.C. et al., "Synthesis of 2-tetralones via a novel 1,2-carbonyl transposition of 1-tetralones," Tetra. Lett. (1996) 37:3243-3246.

Tang, W. et al., "New chiral phosphorus ligands for enantioselective hydrogenation," Chem. Rev. (2003) 103:3029-3069.

\* cited by examiner

PROCESS FOR PREPARING BICYCLIC AMINE DERIVATIVES

CROSS-REFERENCE TO RELATED APPLICATIONS(S)

This claims priority to U.S. Provisional Patent Application No. 61/668,220, filed on Jul. 5, 2012.

BACKGROUND OF THE INVENTION

The present invention relates to a process for preparing bicyclic amine derivatives such 2-aminotetralines, 2-aminoindanes, 3-aminochromanes, 3-aminothiochromanes or 3-amino-1,2,3,4-tetrahydroquinolines by asymmetric hydrogenation of the corresponding enamines. The invention also relates to intermediates of said process.

Certain 1-substituted 2-aminotetraline and 2-aminoindanes and 4-substituted 3-aminochromane, 3-aminothiochromane and 3-amino-1,2,3,4-tetrahydroquinoline derivatives are of great interest as pharmaceutical agents or their synthetical precursors. Such derivatives have been described in WO 00/20376, for instance, as ligands for the neuropeptide Y receptor of subtype Y5, and in WO 2010/092180 and WO 2012/020131 as inhibitors of glycine transporter 1. However, for preparing these compounds in high chiral purity the aforementioned documents only disclose multi-step processes that require chiral separation of enantiomeric mixtures.

While the catalytic enantioselective hydrogenation of enamines is a known process, there are only few pior art reports on the asymmetric hydrogenation of cyclic enamines that have a tetrasubstituted double bound and an exocyclic amino group.

Ma et al., Tetrahedron: Asymmetry, 2011, 22, 506-511, describe rhodium-catalyzed asymmetric hydrogenations of 1-acetylamino-2-cyano-cyclopentene and -cyclohexene using bisphosphine ligands. The resulting cis-1-acetylamino-2-cyano-cyclopentane and -cyclohexane were obtained in high yields but only poor to moderate enantioselectivities.

Similarly, Lucarini et al., Chem. Asian J., 2010, 5, 550-554, report on diastereoselective syntheses of cis-4-phenyl-2-propionamido-tetraline via hydrogenation of racemic N-(4-phenyl-3,4-dihydronaphthalen-2-yl)propionamide which was catalyzed by rhodiumcomplexes including chiral phosphine ligands. However, only poor enantioselectivities could be achieved.

It is an object of the present invention to provide a process that is suitable for the enantioselective preparation of 1-substituted 2-aminotetraline and aminoindane derivatives as well as of 4-substituted 3-aminochromane, 3-aminothiochromane or 3-amino-1,2,3,4-tetrahydroquinoline derivatives. This process should be simple to carry out, based on selective reactions and suitable for the production on an industrial scale.

The object is achieved by the process described in detail below.

SUMMARY OF THE INVENTION

The present invention provides a process for preparing a bicyclic amine derivative of the formula (Ia) or (Ib),

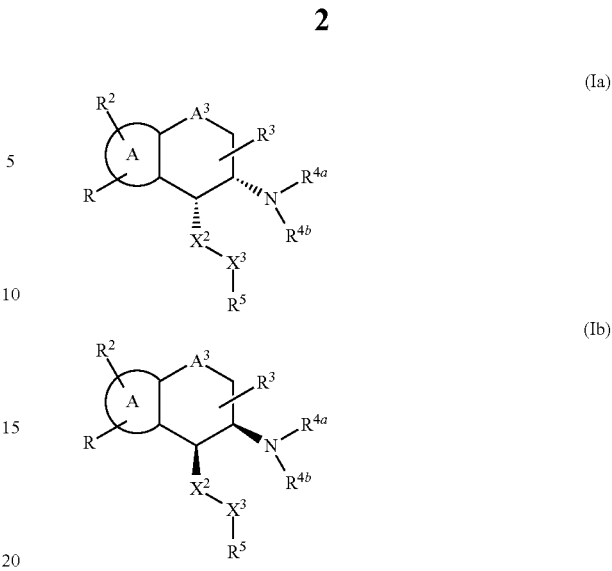

wherein

A is a 5- or 6-membered ring;

R is hydrogen, halogen, —CN, hydroxyl which optionally carries a protecting group, a group Y'-$A^2$-$X^1$—, or a group $R^1$—W-$A^1$-Q-Y-$A^2$-$X^1$—;

$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl) aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

W is —$NR^8$— or a bond;

$A^1$ is optionally substituted alkylene or a bond;

Q is —$S(O)_2$— or —C(O)—;

Y is —$NR^9$— or a bond;

Y' is Y which optionally carries a protecting group;

$A^2$ is optionally substituted alkylene, alkylene-CO—, —CO-alkylene, alkylene-O-alkylene, alkylene-$NR^{10}$-alkylene, optionally substituted alkenylene, optionally substituted alkynylene, optionally substituted arylene, optionally substituted heteroarylene or a bond;

$X^1$ is —O—, —NR$^{11}$—, —S—, optionally substituted alkylene, optionally substituted alkenylene, optionally substituted alkynylene;

$R^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form a 5- or 6-membered ring;

$A^3$ is —O—, —S—, —NR$^{16}$—, a bond or alkylene;

$R^3$ is hydrogen, halogen, alkyl or alkoxy, or two radicals $R^3$ together with the carbon atom to which they are attached form a carbonyl group;

$R^{4a}$ is alkylcarbonyl, halogenated alkylcarbonyl or arylcarbonyl;

$R^{4b}$ is hydrogen or alkyl; or $R^{4a}$, $R^{4b}$
together are alkylenecarbonyl;

$X^2$ is —O—, —NR$^6$—, —S—, >CR$^{12a}$R$^{12b}$ or a bond;

$X^3$ is —O—, —NR$^7$—, —S—, >CR$^{13a}$R$^{13b}$ or a bond;

$R^5$ is optionally substituted aryl, optionally substituted cycloalkyl or optionally substituted heterocyclyl;

$R^6$ is hydrogen or alkyl;

$R^7$ is hydrogen or alkyl;

$R^8$ is hydrogen or alkyl;

$R^9$ is hydrogen, alkyl, cycloalkyl, aminoalkyl, optionally substituted arylalkyl or heterocyclyl; or $R^9$, $R^1$
together are alkylene; or $R^9$ is alkylene that is bound to a carbon atom in $A^2$ and $A^2$ is alkylene or to a carbon atom in $X^1$ and $X^1$ is alkylene;

$R^{10}$ is hydrogen, alkyl or alkylsulfonyl;

$R^{11}$ is hydrogen or alkyl, or $R^9$, $R^{11}$
together are alkylene, $R^{12a}$ is hydrogen, optionally substituted alkyl, alkylaminoalkyl, dialkylaminoalkyl, heterocyclylalkyl, optionally substituted aryl or hydroxy;

$R^{12b}$ is hydrogen or alkyl, or $R^{12a}$, $R^{12b}$
together are carbonyl or optionally substituted alkylene, wherein one —CH$_2$— of alkylene may be replaced by an oxygen atom or —NR$^{14}$—;

$R^{13a}$ is hydrogen, optionally substituted alkyl, alkylaminoalkyl, dialkylaminoalkyl, heterocyclylalkyl, optionally substituted aryl or hydroxy;

$R^{13b}$ is hydrogen or alkyl, or $R^{13a}$, $R^{13b}$
together are carbonyl or optionally substituted alkylene, wherein one —CH$_2$— of alkylene may be replaced by an oxygen atom or —NR$^{15}$—;

$R^{14}$ is hydrogen or alkyl;

$R^{15}$ is hydrogen or alkyl; and $R^{16}$ is hydrogen, alkyl, cycloalkylalkyl, halogenated alkyl, hydroxyalkyl, alkoxyalkyl, aminoalkyl, CH$_2$CN, arylalkyl, cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl, or a salt thereof, comprising the rhodium-catalyzed asymmetric hydrogenation of an enamine of the formula (II),

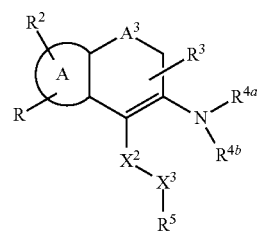

(II)

wherein A, $A^3$, R, $R^2$, $R^3$, $R^{4a}$, $R^{4b}$, $R^5$, $X^2$ and $X^3$ are as defined above, or of a salt thereof, in the presence of a chiral ligand, wherein the chiral ligand is a chiral phosphine ligand.

The terms aminotetraline, aminochromane, aminothiochromane and amino-1,2,3,4-tetrahydroquinoline derivative are used herein to denote in particular aminotetralines ($A^3$ is —CH$_2$—), aminochromanes ($A^3$ is —O—), thiochromanes ($A^3$ is —S—) and 1,2,3,4-tetrahydroquinolines ($A^3$ is —NR$^{16}$—) as well as aminoindanes ($A^3$ is a bond), benzocycloheptanes ($A^3$ is —CH$_2$—CH$_2$—), and also fused $C_5$-$C_7$-cycloalkanes, tetrahydropyranes, tetrahydrothiopyranes and tetrahydropyridines wherein the benzene ring of the tetralines, chromanes, thiochromanes, 1,2,3,4-tetrahydroquinolines, indanes and benzocycloheptanes is replaced by a 5- or 6-membered heterocyclic ring.

In addition, the present invention relates to a process for preparing the bicyclic amine derivative of the formula (Ia) or (Ib), comprising:

(a) providing a ketone of the formula (V),

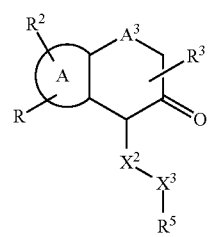

(V)

wherein A, $A^3$, R, $R^2$, $R^3$, $R^5$, $X^2$ and $X^3$ are as defined herein;

(b) converting the ketone of the formula (V) into the enamine of the formula (II); and (c) converting the enamine of the formula (II) into the bicyclic amine derivatives of the formula (Ia) or (Ib) as described herein.

The present invention further relates to a bicyclic amine derivative of the formula (Ia) or the formula (Ib),

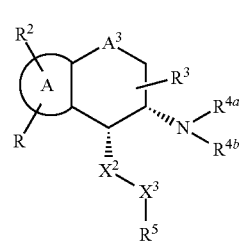

(Ia)

-continued

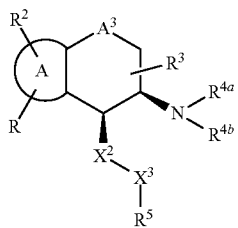

(Ib)

wherein
A, A³, R, R², R³, R⁴ᵃ, R⁴ᵇ, R⁵, X² and X³ are as defined herein.

The present invention further relates to an enamine of the formula (II),

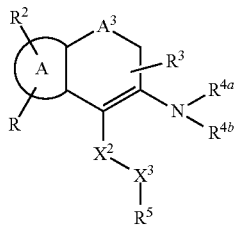

(II)

wherein A, A³, R, R², R³, R⁴ᵃ, R⁴ᵇ, R⁵, X² and X³ are as defined herein.

The present invention also relates to a ketone of the formula (V'),

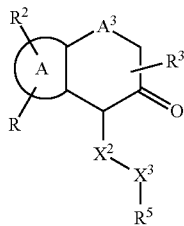

(V')

wherein A, A³, R², R³, R⁵, X² and X³ are as defined herein and R is halogen, methoxymethoxy, methoxyethoxymethoxy, tert-butyloxy, allyloxy, 2-tetrapyranyloxy, benzyloxy, acetyloxy, pivaloyloxy, benzoyloxy, tert-butyldimethylsilyloxy or tert-butyldiphenylsilyloxy, preferably halogen and in particular bromine.

DETAILED DESCRIPTION OF THE INVENTION

Suitable rhodium catalysts for the asymmetric hydrogenation of the process according to the invention are rhodium compounds which include rhodium in the oxidation state 0, 1, 2 or 3. Preferably the rhodium is in the oxidation state 1, i.e. the rhodium catalyst is a rhodium(I) compound.

If rhodium compounds with rhodium in an oxidation state different from 1 are used, they have to be transformed, either before or during the asymmetric hydrogenation of the inventive process, into rhodium compounds with rhodium being in the oxidation state 1.

The asymmetric hydrogenation of the inventive process is accomplished by using said rhodium catalyst and a chiral phosphine ligand in combination. Thus, the catalytic system of the process according to the invention is characterized in that it comprises a rhodium catalyst, which is preferably a rhodium(I) compound, and a chiral phosphine ligand.

The catalytic system of the inventive process can be employed in the form of a preformed rhodium complex which comprises the rhodium compound and the chiral phosphine ligand. Alternatively, the catalytic system is formed in situ in the reaction mixture by combining a rhodium compound, herein also termed pre-catalyst, with the chiral phosphine ligand and optionally one or more further suitable ligands to give a catalytically active rhodium complex in the reaction mixture.

According to a particular embodiment of the invention the catalytic system is formed in situ by combining a pre-catalyst with a chiral phosphine ligand.

Suitable pre-catalysts are selected from neutral rhodium complexes, oxides and salts of rhodium. Rhodium compounds that are useful as pre-catalyst are in particular rhodium(I) compounds of the formula (IIIa), (IIIb) or (IIIc),

[Rh Li¹ An]₂ (IIIa)

[Rh Li²₂ An]ₙ (IIIb)

[Rh Li¹₂ An] (IIIc)

wherein
Li¹ is $C_5$-$C_{12}$-alkadiene, $C_5$-$C_{12}$-cycloalkadiene or $C_5$-$C_{12}$-bicycloalkadiene, preferably $C_5$-$C_{12}$-cycloalkadiene or $C_5$-$C_{12}$-bicycloalkadiene, in particular cylcopentadiene, norbornadiene (NBD) or 1,5-cyclooctadiene (COD), and specifically norbornadiene or 1,5-cyclooctadiene;
Li² is $C_2$-$C_{12}$-alkene or $C_5$-$C_8$-cycloalkene, in particular allyl or cis-cyclooctene (coe), and specifically cis-cyclooctene;
n is 1 or 2; and
An is halide, tetrafluoroborate, trifluoromethanesulfonate or acetylacetonate (acac), in particular halide, tetrafluoroborate or trifluoromethanesulfonate and specifically chloride.

According to a particular embodiment of the invention a pre-catalyst of the formula (IIIa) with Li¹ being $C_6$-$C_{10}$-cycloalkadiene or $C_6$-$C_{10}$-bicycloalkadiene, in particular 1,5-cyclooctadiene or norbornadiene, and An being chloride, is used in the inventive process. Thus, if Li¹ is 1,5-cyclooctadiene or norbornadiene, according to this embodiment the pre-catalyst has the formula [Rh(COD)Cl]₂ or the formula [Rh(NBD)Cl]₂.

According to a further particular embodiment of the invention a pre-catalyst of the formula (IIIb) with Li² being $C_5$-$C_8$-cycloalkene, in particular cis-cyclooctene, and An being chloride or acetoacetonate, is used in the inventive process. Thus, if Li² is cis-cyclooctene, according to this embodiment the precatalyst may have the formula [Rh(coe)₂Cl]₂ or the formula [Rh(coe)₂(acac)].

According to a particular embodiment of the invention a pre-catalyst of the formula (IIIc) with Li¹ being $C_6$-$C_{10}$-cycloalkadiene or $C_6$-$C_{10}$-bicycloalkadiene, in particular 1,5-cyclooctadiene or norbornadiene, and An being tetrafluoroborate, is used in the inventive process. Thus, if Li¹ is 1,5-cyclooctadiene or norbornadiene, according to this embodiment the precatalyst has the formula [Rh(COD)₂BF₄] or the formula [Rh(NBD)₂BF₄].

Particularly preferred pre-catalysts for the in situ formation of the catalytic system according to the inventive process are [Rh(COD)Cl]₂ and [Rh(NBD)Cl]₂.

Chiral phosphine ligands known in the art, as described for example in "New Chiral Phosphorus Ligands for Enantioselective Hydrogenation", W. Tang and X. Zhang, Chem. Rev. 2003, 103, 3029-3069 are suitable, as part of the catalytic system, for the asymmetric hydrogenation of the inventive process. Preferred in this regard are chiral phosphine ligands having at least one chiral center which preferably is a carbon atom.

According to an embodiment of the invention the chiral phosphine ligand of the inventive process is a diphosphine ligand, i.e. it comprises two phosphine groups.

According to a preferred embodiment of the invention the chiral phosphine ligand of the inventive process is a diphosphine ligand comprising a ferrocene moiety. Such a ligand preferably has one of the following formulae (IVa), (IVb), (IVc) and (IVd):

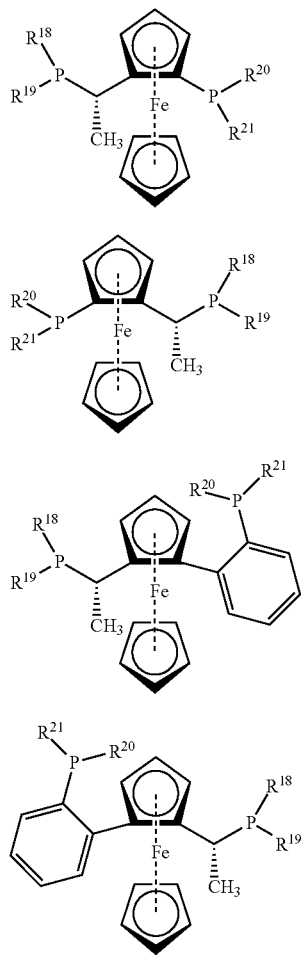

wherein
$R^{18}$, $R^{19}$, $R^{20}$ and $R^{21}$, independently of each other, are selected from the group consisting of $C_1$-$C_{12}$-alkyl (e.g. methyl, ethyl, isopropyl or tert-butyl), $C_5$-$C_7$-cycloalkyl (e.g. cyclopentyl or cyclohexyl), optionally substituted $C_3$-$C_6$-hetaryl (e.g. furyl) and optionally substituted $C_6$-$C_{12}$-aryl (e.g. phenyl, 3-methylphenyl, 4-methoxyphenyl, 4-dimethylaminophenyl, 1-naphthyl or 2-naphthyl).

In connection with $R^{18}$, $R^{19}$, $R^{20}$ and $R^{21}$, substituted $C_6$-$C_{12}$-aryl in particular includes $C_6$-$C_{12}$-aryl substituted with 1, 2, 3, 4 or 5 and more preferably with 1, 2 or 3 substituents selected from the group consisting of $C_1$-$C_4$-alkyl, $C_1$-$C_4$-alkoxy and di-$C_1$-$C_4$-alkylamine.

In connection with $R^{18}$, $R^{19}$, $R^{20}$ and $R^{21}$, substituted $C_3$-$C_6$-hetaryl in particular includes $C_3$-$C_6$-hetaryl substituted with 1, 2, 3, 4 or 5 and more preferably with 1, 2 or 3 substituents selected from the group consisting of $C_1$-$C_4$-alkyl, $C_1$-$C_4$-alkoxy and di-$C_1$-$C_4$-alkylamine.

According to a preferred embodiment of the invention the radicals $R^{18}$ and $R^{19}$ of the chiral diphosphine ligand of formula (IVa), (IVb), (IVc) or (IVd) have the same meaning. In case the chiral diphosphine ligand is of formula (IVa) or (IVb) $R^{18}$ and $R^{19}$ in particular both represent the same $C_1$-$C_8$-alkyl moiety (e.g. methyl, ethyl, n-propyl, isopropyl, n-butyl, isobutyl, 2-butyl, tert-butyl, n-pentyl, n-hexyl, n-heptyl or n-octyl), and specifically both represent tert-butyl. In case the chiral diphosphine ligand is of formula (IVc) or (IVd) $R^{18}$ and $R^{19}$ in particular both represent the same $C_1$-$C_8$-alkyl moiety (e.g. methyl, ethyl, n-propyl, isopropyl, n-butyl, isobutyl, 2-butyl, tert-butyl, n-pentyl, n-hexyl, n-heptyl or n-octyl) or the same optionally substituted $C_6$-$C_{10}$-aryl moiety (e.g. phenyl, 3-methylphenyl, 4-methoxyphenyl, 4-dimethylaminophenyl or naphthyl).

According to a further preferred embodiment of the invention the radicals $R^{20}$ and $R^{21}$ of the chiral diphosphine ligand of formula (IVa), (IVb), (IVc) or (IVd) have the same meaning. More preferably, $R^{20}$ and $R^{21}$ both represent the same optionally substituted $C_3$-$C_5$-hetaryl moiety (e.g. 2-furyl) or the same optionally substituted $C_6$-$C_{10}$-aryl moiety (e.g. phenyl, 3-methylphenyl, 3,5-dimethylphenyl, 4-methoxyphenyl, 4-dimethylaminophenyl, 1-naphthyl, 2-naphthyl, 5-methyl-1-naphthyl or 6-methoxy-1-naphthyl), in particular both represent 2-furyl, optionally substituted phenyl or 1-naphthyl and specifically phenyl or 1-naphthyl.

According to a particular embodiment of the invention in the chiral diphosphine ligand of formula (IVa) or (IVb) the radicals $R^{18}$ and $R^{19}$ both represent the same $C_1$-$C_8$-alkyl moiety, in particular tert-butyl, and the radicals $R^{20}$ and $R^{21}$ both represent the same optionally substituted $C_6$-$C_{10}$-aryl moiety, in particular 1-naphthyl.

According to a further particular embodiment of the invention in the chiral diphosphine ligand of formula (IVc) or (IVd) the radicals $R^{18}$, $R^{19}$, $R^{20}$ and $R^{21}$ all represent the same $C_1$-$C_8$-alkyl moiety, in particular tert-butyl, or the same optionally substituted $C_6$-$C_{10}$-aryl moiety, in particular optionally substituted phenyl or 1-naphthyl.

According to a further particular embodiment of the invention the chiral diphosphine ligand of formula (IVa) or (IVc), and preferably the chiral diphosphine ligand of formula (IVa), is used as part of the catalytic system in the asymmetric hydrogenation of the invention for the enantioselective preparation of the bicyclic amine derivative of the formula (Ia).

According to a yet further particular embodiment of the invention the chiral diphosphine ligand of formula (IVb) or (IVd), and preferably the chiral diphosphine ligand of formula (IVb), is used as part of the catalytic system in the asymmetric hydrogenation of the invention for the enantioselective preparation of the bicyclic amine derivative of the formula (Ib).

The inventive conversions described hereinafter are performed in reaction vessels customary for such reactions, the reaction being configurable in a continuous, semicontinuous or batchwise manner. In general, the particular reactions will be performed under atmospheric pressure, under reduced pressure or increased pressure. As described in detail below, the asymmetric hydrogenation of the inventive process is usually carried out under increased pressure.

The conversion of the process according to the invention for preparing a bicyclic amine derivative of the formula (Ia) or (Ib) is an asymmetric hydrogenation reaction leading to the transformation of the double bond of the enamine group into a single bond with the substituents —$X^2$—$X^3$—$R^5$ and $N(R^{4a})R^{4b}$ being in the cis-configuration. The reaction is carried out by contacting an enamine of the formula (II) with a catalytic system comprising a rhodium catalyst and a chiral phosphine ligand usually in a solvent under a hydrogen atmosphere using suitable reaction conditions.

In general, the asymmetric hydrogenation is performed under temperature control. The reaction is typically effected in a closed reaction vessel with stirring and heating apparatus.

The enamine II and the catalytic system can in principle be contacted with one another in any desired sequence. For example, the catalytic system, if appropriate dissolved in a solvent or in dispersed form, can be initially charged and admixed with the enamine II or, conversely, the enamine II, if appropriate dissolved in a solvent or in dispersed form, can be initially charged and admixed with the catalytic system. Alternatively, these two components can also be added simultaneously to the reaction vessel. The hydrogen atmosphere can be established before or after the addition of the catalytic system or else together with it. Moreover, as an alternative to their joint addition in the form of a preformed catalytic complex the two components of the catalytic system, i.e. the chiral phosphine ligand and the rhodium compound, can be added separately to the reaction vessel. This means that the two components are added independently of one another to the reaction vessel before or after the addition of the enamine II or else together with the enamine II.

According to a particular embodiment of the invention the chiral phosphine ligand and the rhodium compound, that are both included in the catalytic system of the inventive process, are charged separately to the reaction vessel.

The rhodium complex including the chiral phosphine ligand, in case it is preformed, or the rhodium compound of the catalytic system, in case of an in situ formation, is used in the process according to the invention preferably in an amount of 0.05 to 8.0 mol-%, more preferably in an amount of 0.1 to 5.0 mol-%, particularly in an amount of 0.1 to 3.0 mol-% and specifically in an amount of 0.15 to 2.0 mol-%, based on the relation of the moles of rhodium to the moles of enamine II.

In case the catalytic complex is formed in situ the chiral phosphine ligand is added to the reaction mixture of the inventive asymmetric hydrogenation preferably in an amount of 30 to 240 mol-%, more preferably in an amount of 40 to 200 mol-%, in particular in an amount of 45 to 150 mol-% and specifically in an amount of 50 to 120 mol-%, based on the relation of the moles of chiral phosphine ligand to the moles of rhodium.

It has been found to be appropriate to initially charge the reaction vessel with a rhodium compound, a chiral phosphine ligand and an enamine II either jointly or successively and then establish inert conditions, in particular by exchanging the atmosphere to nitrogen or argon. The solvent, which has preferably been degassed, is typically added thereafter to the reaction vessel. Afterwards the resulting mixture is preferably agitated for about 1 min to 1 hour, preferably for 5 to 40 min, at a temperature of about 20 to 70° C., preferably of 30 to 60° C., under an inert atmosphere. This pretreatment may be carried out at ambient pressure or by pressurizing the reactor to up to 80 psig, preferably up to 60 psig, with the inert gas. The rationale for this pretreatment is that it may further the formation of a rhodium complex that includes the chiral phosphine ligand and possibly also includes the enamine II.

It has further been found to be appropriate, either immediately after the addition of the solvent or preferably after the aforementioned pretreatment, to exchange the inert gas with hydrogen and pressurize the reactor with hydrogen to the desired degree.

The hydrogen pressure of the asymmetric hydrogenation of the inventive process is determined by several factors, for example the reactivity of the enamine II employed, the type of the catalytic system selected and the reaction temperature, and can be determined by the person skilled in the art in the individual case, for example by simple preliminary tests. In general, the asymmetric hydrogenation is performed with the reactor being pressurized with hydrogen to at least 40 psig, preferably to at least 50 psig, more preferably to at least 55 psig, for example to 40 to 100 psig, in particular to 50 to 80 psig and specifically to 55 to 70 psig.

Likewise, the temperature of the asymmetric hydrogenation of the inventive process is determined by several factors, for example the reactivity of the enamine II employed, the type of the catalytic system selected and the reaction pressure, and can be determined by the person skilled in the art in the individual case, for example by simple preliminary tests. In general, the asymmetric hydrogenation of the process according to the invention is performed at a temperature in the range from 35 to 100° C., preferably in the range from 45 to 80° C. and specifically in the range from 50 to 75° C.

Suitable solvents for the asymmetric hydrogenation of the inventive process depend in the individual case on the selection of the particular reactants and reaction conditions. It has generally been found to be advantageous to use a polar organic solvent which may be selected from protic or aprotic solvents or mixtures thereof, with protic solvents being preferred. Useful polar aprotic organic solvents here include, for example, halogenated alkanes, such as methylene chloride, chloroform or 1,2-dichlorethane, substituted aromatic hydrocarbons, such as toluene, the xylenes, mesitylene or chlorobenzene, aliphatic $C_3$-$C_8$-ethers, such as 1,2-dimethoxyethane (DME), diethylene glycol dimethyl ether (diglyme), diethyl ether, diisopropyl ether, methyl isobutyl ether, methyl tert-butyl ether and ethyl tert-butyl ether, alicyclic $C_3$-$C_6$-ethers, such as tetrahydrofuran (THF), tetrahydropyran, 2-methyltetrahydrofuran, 3-methyltetrahydrofuran and 1,4-dioxane, short-chain ketones, such as ethyl methyl ketone and isobutyl methyl ketone, esters, such as ethyl acetate or ethyl propionate, amides, such as N,N-dimethylformamide (DMF), N,N-dimethylacetamide or N-methylpyrrolidone (NMP), pyridines, such as pyridine, 2,6-dimethylpyridine or 2,4,6-trimethylpyridine, dimethyl sulfoxide (DMSO), acetonitrile, or mixtures of these solvents with one another. Useful polar protic organic solvents here include $C_1$-$C_4$-alkanols, such as methanol, ethanol, propanol or isopropanol, $C_2$-$C_4$-alkandiols, such as ethylene glycol or propylene glycol, ether alkanols, such as diethylene glycol, sulfoxides, such as dimethyl sulfoxide, and mixtures thereof. Preferably the asymmetric hydrogenation of the inventive process is carried out in a polar protic organic solvent or in a solvent mixture including such solvents. According to a particular embodiment of the invention said hydrogenation is carried out in methanol or ethanol and preferably in methanol.

In general, the solvent is used in the asymmetric hydrogenation of the inventive process in a total amount that typically is in the range from 500 to 20000 g and preferably in the range from 1000 to 5000 g, based on 1 mol of the enamine II.

Preference is given to using solvents which are essentially anhydrous, i.e. have a water content of less than 1000 ppm and especially not more than 100 ppm.

The bicyclic amine derivative of the formula (Ia) or (Ib) formed in the asymmetric hydrogenation according to the inventive process can be isolated from the reaction mixture by customary work-up procedures, e.g. by filtration, such as filtration through a fibrous filter cartridge, a membrane filter or a pad of celite, removing the solvent, e.g. under reduced pressure, slurrying, such as slurrying in a hot apolar solvent, or by a combination of these measures. Preferably the reaction mixture from the inventive asymmetric hydrogenation is worked-up, after an optional filtration step, by concentration to remove at least most of the solvent, slurrying the resulting residue in a suitable solvent, e.g. hot heptane, and then filtering off and drying the obtained product. Further purification can be effected by procedures known in the art, for example crystallization or chromatography. However, typically the product is already obtained in a purity which does not require further purification steps.

According to a particular embodiment, the process as disclosed herein further comprises crystallizing from heptane, methanol or a mixture of heptane and methanol the compound of formula (Ia) or (Ib), wherein A is a benzene ring, R is —OCH$_3$, R$^2$ is hydrogen, A$^3$ is —CH$_2$—, R$^3$ is hydrogen, R$^{4a}$ is ethoxycarbonyl, R$^{4b}$ is hydrogen, X$^2$ is —CH$_2$—, X$^3$ is a bond, and R$^5$ is phenyl. For instance, the crude product of formula (Ia), wherein A is a benzene ring, R is —OCH$_3$, R$^2$ is hydrogen, A$^3$ is —CH$_2$—, R$^3$ is hydrogen, R$^{4a}$ is ethoxycarbonyl, R$^{4b}$ is hydrogen, X$^2$ is —CH$_2$—, X$^3$ is a bond, and R$^5$ is phenyl, is concentrated to remove at least most of the solvent, e.g. methanol, the resulting residue is slurried in a suitable solvent, e.g. hot heptane, and then the obtained product is filtered off and dried. In this way, the optical purity of the crude product of formula (Ia) can be increased to above 98% ee. On the other hand, the product of formula (Ib), wherein A is a benzene ring, R is —OCH$_3$, R$^2$ is hydrogen, A$^3$ is —CH$_2$—, R$^3$ is hydrogen, R$^{4a}$ is ethoxycarbonyl, R$^{4b}$ is hydrogen, X$^2$ is —CH$_2$—, X$^3$ is a bond, and R$^5$ is phenyl, can be obtained in high optical purity by crystallization from methanol.

Starting from enamines of formula (II) the asymmetric hydrogenation of the process according to the invention allows for the efficient preparation of bicyclic amine derivatives of the formula (Ia) or (Ib) in excellent yields and enantioselectivities.

In a further aspect the present invention relates to a process for preparing the bicyclic amine derivative of the formula (Ia) or (Ib), which process comprises the following steps (a) to (c):
(a) providing a ketone of the formula (V),

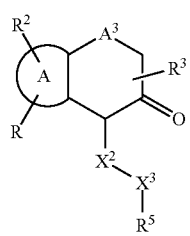

(V)

wherein A, A$^3$, R, R$^2$, R$^3$, R$^5$, X$^2$ and X$^3$ are as defined herein and in particular have one of the meanings mentioned herein as preferred;
(b) converting the ketone of the formula (V) into the enamine of the formula (II); and
(c) converting the enamine of the formula (II) into the bicyclic amine derivatives of the formula (Ia) or (Ib) in the presence of a chiral phosphine ligand via the rhodium-catalyzed asymmetric hydrogenation according to the inventive process described herein above.

This process comprising steps (a) to (c) is hereinafter also termed "process A".

In process A the ketone of the formula (V) is provided in step (a). The ketone of the formula (V) can be prepared, for example, starting from the corresponding ketone of the formula (VIII).

(VIII)

A ketone V can be obtained from the corresponding ketone VIII, for instance, by electrophilically adding a substituent —X$^2$—X$^3$—R$^5$ to the double bond of the enamine that is intermediately formed from the ketone VIII, according to established method well-known in the art. A corresponding benzylation of a ketone VIII via enamine alkylation is described, for example, in WO 2010/092180.

Ketones of the formula (VIII) are commercially available or can be prepared by customary processes. Tetralin-2-one derivatives, for instance, are obtainable via a 1,2-carbonyl transposition of the corresponding tetralin-1-one derivatives according to the procedure disclosed in D. C. Pryde et al., Tetrahedron Letters, 1996, 37, 3243-3246.

In step (b) of process A the ketone of formula (V) is converted into an enamine of the formula (II). This conversion may be achieved by standard methods known in the art for preparing enamines from the corresponding ketones.

Typically the conversion in step (b) is accomplished by reacting the ketone of the formula (v) with an amine of the formula HN(R$^{4a}$)R$^{4b}$ in the presence of an acid.

Suitable acids in this regard include p-toluenesulfonic acid, benzenesulfonic acid, phosphoric acid and hydrochloric acid with preference given to p-toluenesulfonic acid. It may be possible to use the acid in catalytical amounts. Usually, however, it is beneficial to perform the reaction with 0.01 to 0.5 mol acid per mol of the ketone of formula (V). Preferably the amount of acid is 0.05 mol to 0.4 mol, and in particular 0.1 mol to 0.25 mol per mol of the compound of formula (II).

The amine HN(R$^{4a}$)R$^{4b}$ is generally used in amounts of 1 to 5 mols, preferably 1.5 to 4 mols and in particular 2 to 3 mols per mol of the ketone of the formula (V).

The conversion in step (b) is typically performed at temperatures exceeding 50° C., for example at a temperature in the range from 50 to 180° C., preferably from 60 to 150° C. and especially from 80 to 130° C.

It has generally been found to be advantageous to perform the conversion of step (b) in an organic solvent which is sufficiently inert against acids under the reaction conditions. Useful organic solvents here include ethers, for example, aliphatic C$_4$-C$_{10}$-ethers having 1, 2, 3, or 4 oxygen atoms, such as glyme, diglyme, triglyme, diethyl ether, dipropyl ether, methyl isobutyl ether, tert-butyl methyl ether and tert-butyl ethyl ether, alicyclic C$_5$-C$_6$-ethers, such as tetrahydropyrane, 2-methyltetrahydrofurane, 3-methyltetrahydrofurane and 1,4-dioxane, N,N-dimethylamides of C$_1$-C$_4$carboxylic acids, such as dimethylformamide and dimethyl acetamide, N—C$_1$-C$_4$-alkyllactames such as N-methylpyrrolidone, dipolar aprotic solvents such as acetonitrile or dimethylsulfoxide, aliphatic, cycloaliphatic or aromatic hydrocarbons, such as heptanes, cyclohexane, methylcyclohexane, ethylcyclohexane, benzene, toluene, the xylenes and mesitylene, or mixtures of these solvents with one another. Particularly preferred are the aforementioned ethers, the dipolar aprotic solvents, the amides, the lactames and mixtures thereof with aromatic hydrocarbons, as well as the aromatic hydrocarbons. According to a particular embodiment, step (b) is performed in an aromatic hydrocarbon or hydrocarbon mixture, specifically in toluene.

According to one embodiment of the invention the conversion of step (b) is carried out in refluxing solvent, wherein the solvent has a boiling point of 80 to 130° C. According to a particular embodiment the conversion is carried out in refluxing toluene.

The work-up of the reaction mixtures obtained from the conversion in step (b) and the isolation of the enamine of formula (II) is effected in a customary manner, for example by an aqueous extractive work-up, by removing the solvent, e.g. under reduced pressure, by precipitation, e.g. via adding a polar solvent, or a combination of these measures, and optionally subsequent crystallisation or chromatography.

Typically the reaction mixture resulting from the conversion of step (b), for work-up, is cooled down, for instance to ambient temperature, and precipitating product is filtered off. To the concentrated filtrate may then be added a polar organic solvent, such as isopropanol, and the resulting suspension may be cooled down, e.g. to about 0° C., and agitated at that temperature to obtain additional precipitated product that can be filtered off. Further product may precipitate from the resulting filtrate following treatment with polar organic solvent, e.g. a 50:50 (v/v) mixture of isopropanol and ethanol. Combining the precipitates affords the crude enamine II which, if required, may be subjected to further purification steps, such as in particular crystallization.

In addition, the present invention relates to a bicyclic amine derivative of the formula (Ia) or the formula (Ib):

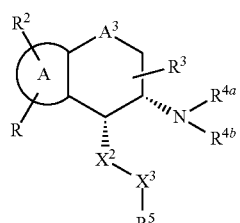

(Ia)

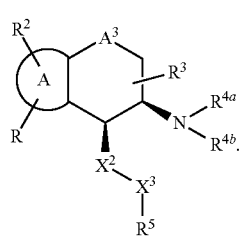

(Ib)

In formulae (Ia) and (Ib) the variables A, $A^3$, R, $R^2$, $R^3$, $R^{4a}$, $R^{4b}$, $R^5$, $X^2$ and $X^3$ are as defined herein and in particular have one of the meanings mentioned herein as preferred.

Particularly preferred bicyclic amine derivatives of the formula (Ia) or the formula (Ib) are those of the formula (Ia') or the formula (Ib'), respectively,

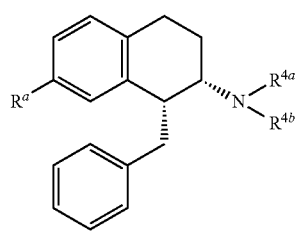

(Ia')

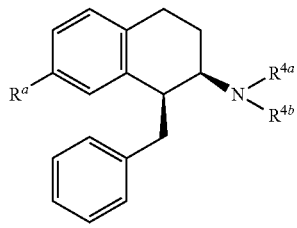

(Ib')

wherein $R^a$ is halogen, in particular bromine, or $C_1$-$C_4$-alkoxy, in particular methoxy;

$R^{4a}$ is $C_1$-$C_4$-alkylcarbonyl, in particular ethylcarbonyl;

$R^{4b}$ is hydrogen; or $R^{4a}$, $R^{4b}$ together are $C_2$-$C_6$-alkylenecarbonyl, in particular 2-ethylenecarbonyl, 3-propylenecarbonyl or 4-butylenecarbonyl.

The present invention also relates to enamines of the formula (II),

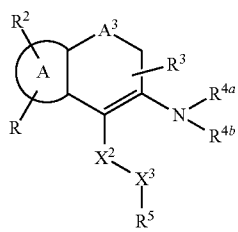

(II)

wherein the variables A, $A^3$, R, $R^2$, $R^3$, $R^{4a}$, $R^{4b}$, $R^5$, $X^2$ and $X^3$ are as defined herein and in particular have one of the meanings mentioned herein as preferred.

Particularly preferred enamines of the formula (II) are those of the formula (II'),

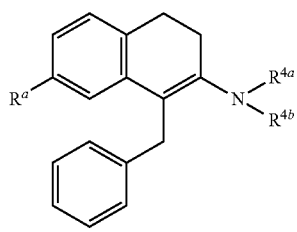

(II')

wherein $R^a$ is halogen, in particular bromine, or $C_1$-$C_4$-alkoxy, in particular methoxy;

$R^{4a}$ is $C_1$-$C_4$-alkylcarbonyl, in particular ethylcarbonyl;

$R^{4b}$ is hydrogen; or $R^{4a}$, $R^{4b}$ together are $C_2$-$C_6$-alkylenecarbonyl, in particular 2-ethylenecarbonyl, 3-propylenecarbonyl or 4-butylenecarbonyl.

The present invention also relates to a ketone of the formula (V'),

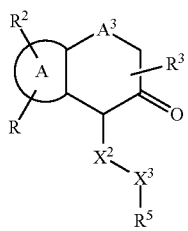

wherein A, $A^3$, $R^2$, $R^3$, $R^5$, $X^2$ and $X^3$ are as defined herein and R is halogen, methoxymethoxy, methoxyethoxymethoxy, tert-butyloxy, allyloxy, 2-tetrapyranyloxy, benzyloxy, acetyloxy, pivaloyloxy, benzoyloxy, tert-butyldimethylsilyloxy or tert-butyldiphenylsilyloxy, preferably halogen and in particular bromine.

A particularly preferred ketone of the formula (V') is that of the formula (V'-1),

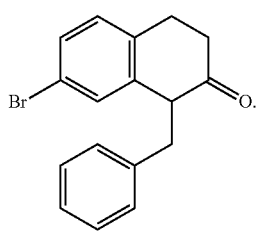

The bicyclic amines of the present invention are or can be converted to further bicyclic 1-substituted 2-aminotetraline and aminoindane derivatives as well as to 4-substituted 3-aminochromane, 3-aminothiochromane or 3-amino-1,2,3,4-tetrahydroquinoline derivatives which are inhibitors of the glycine transporter GlyT1. Such inhibitors and processes for making them are disclosed, for instance, in WO 2010/092180 and WO 2012/020131, the content of which is incorporated herein in its entirety. The inhibitors are useful in inhibiting the glycine transporter; in treating a variety of neurologic and psychiatric disorders, or in treating pain.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy-$C_1$-$C_4$-alkyl, amino-$C_1$-$C_4$-alkyl, $C_1$-$C_4$-alkenyl, oxo (=O), OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, $NH_2$, NH—$C_1$-$C_6$-alkyl, N—$(C_1$-$C_6$-alkyl$)_2$, NH—$(C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_3$-$C_{12}$-heterocyclyl, $SO_2NH$—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, isopropyl, n-butyl, 2-butyl, isobutyl or tert-butyl. $C_1$-$C_2$-Alkyl is methyl or ethyl, $C_1$-$C_3$-alkyl is additionally n-propyl or isopropyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, isopropylaminomethyl, n-butylaminomethyl, 2-butylaminomethyl, isobutylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, isopropylcarbonylaminomethyl, n-butylcarbonylaminomethyl, 2-butylcarbonylaminomethyl, isobutylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, isopropylaminocarbonylaminomethyl, n-butylaminocarbonylaminomethyl, 2-butylaminocarbonylaminomethyl, isobutylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, isopropylsulfonylaminomethyl, n-butylsulfonylaminomethyl, 2-butylsulfonylaminomethyl, isobutylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl)amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_{10}$-Alkylene is straight-chain or branched alkylene group having from 1 to 10 carbon atoms. Examples include methylene, ethylene, 1,2-propylene, 1,3-propylene, 1,4-butylene, 1,4-pentylene, 1,5-pentylene and 1,6-hexylene.

$C_2$-$C_{10}$-Alkylenecarbonyl is a radical of the formula R—C(O)—, wherein R is an alkylene group as defined herein having from 2 to 10, preferably from 2 to 5, in particular from 2 to 4 carbon atoms. Examples include 2-ethylenecarbonyl, 3-propylenecarbonyl, 4-butylenecarbonyl, 4-pentylenecarbonyl, 5-pentylenecarbonyl and 6-hexylenecarbonyl.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, isobutoxy (2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, isopropylaminomethoxy, n-butylaminomethoxy, 2-butylaminomethoxy, isobutylaminomethoxy, tert-butylaminomethoxy, 2-(methylamino)ethoxy, 2-(ethylamino)ethoxy, 2-(n-propylamino)ethoxy, 2-(isopropylamino)ethoxy, 2-(n-butylamino)ethoxy, 2-(2-butylamino)ethoxy, 2-(isobutylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a di-alkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, isopropylcarbonylaminomethoxy, n-butylcarbonylaminomethoxy, 2-butylcarbonylaminomethoxy, isobutylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(isopropylcarbonylamino)ethoxy, 2-(n-butylcarbonylamino) ethoxy, 2-(2-butylcarbonylamino)ethoxy, 2-(isobutylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, isopropoxycarbonylaminomethoxy, n-butoxycarbonylaminomethoxy, 2-butoxycarbonylaminomethoxy, isobutoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(isopropoxycarbonylamino)ethoxy, 2-(n-butoxycarbonylamino)ethoxy, 2-(2-butoxycarbonylamino)ethoxy, 2-(isobutoxycarbonylamino)ethoxy, 2-(tert-butoxycarbonylamino) ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy (2-propen-1-yloxy), 1-propen-1-yloxy, 2-propen-2-yloxy, methallyloxy (2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino) ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino) ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, isopropylaminosulfonyl, n-butylaminosulfonyl, 2-butylaminosulfonyl, isobutylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, isopropylamino, n-butylamino, 2-butylamino, isobutylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido (methylcarbonylamino), propionamido, n-butyramido, 2-methylpropionamido (isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino (2-propen-1-ylamino), 1-propen-1-ylamino, 2-propen-2-ylamino, methallylamino (2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, isopropylsulfonylamino, n-butylsulfonylamino, 2-butylsulfonylamino, isobutylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl (piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-di-hydro-1,2-oxazin-5-yl, 4H-5,6-dihydro-1,2-oxazin-6-yl, 4H-5,6-dihydro- 1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

The salts of the aminotetraline, aminochromane, aminothiochromane and amino-1,2,3,4-tetrahydroquinoline derivatives of the formula (Ia) or (Ib) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the aminochromane, aminothiochromane and amino-1,2,3,4-tetrahydroquinoline derivatives also include salts of a physiologically tolerated anion with aminochromane, aminothiochromane and amino-1,2,3,4-tetrahydroquinoline derivatives wherein one or more than one nitrogen atom is quaternized, e.g. with an alkyl residue (e.g. methyl or ethyl).

In formulae (Ia), (Ib), (II), (V) and (V'), there may be one or more than one substituent R, $R^2$ and/or $R^3$. More particularly, there may be up to 3 substituents $R^2$, and up to 4 substituents $R^3$. Preferably there is one substituent R and 1, 2 or 3 substituents $R^2$. Formula (Ia), for instance, may thus be depicted as follows:

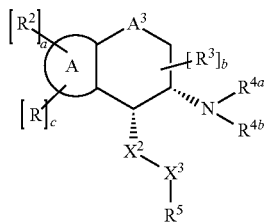

wherein a is 1, 2 or 3, b is 1, 2, 3 or 4 and c is 1. This applies accordingly to formulae (Ib), (II), (V) and (V'). If there is more than one radical $R^2$, these may be the same or different radicals. If there is more than one radical $R^3$, these may be the same or different radicals.

In the compounds of formulae (Ia), (Ib), (II), (V) and (V') A is a 5- or 6-membered ring which includes two carbon atoms from the $C_5$-$C_7$-cycloalkane, tetrahydropyrane, tetrahydrothiopyrane or tetrahydropyridine moiety to which A is fused. A may be a homocyclic or heterocyclic ring. The ring may be saturated, unsaturated non-aromatic or aromatic. According to a particular embodiment, A is a benzene ring. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic rings comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

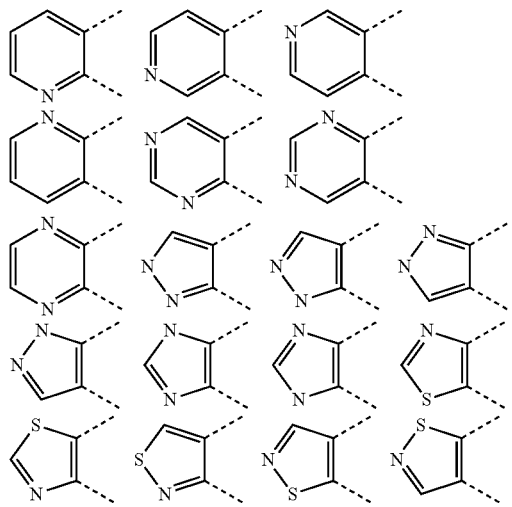

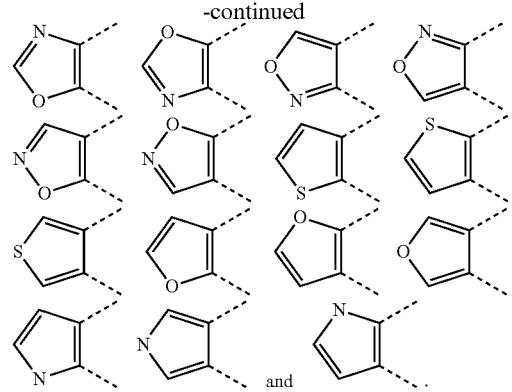

In said formulae, hydrogen atoms are not depicted. This is meant to illustrate that the free valency of a carbon or nitrogen atom may be either bound to a hydrogen atom, to R or to $R^2$. Accordingly, R and $R^2$ may be C- or N-bound at any position of ring A.

The skilled person will appreciate that some of the rings depicted above may be represented with a different structure, e.g. with hydrogen atoms having other positions than those shown above, for instance as given in the following structures:

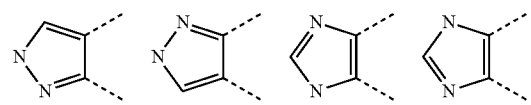

In case A is a heterocyclic ring, it is preferably selected from the group consisting of the following 5- or 6-membered heterocyclic rings:

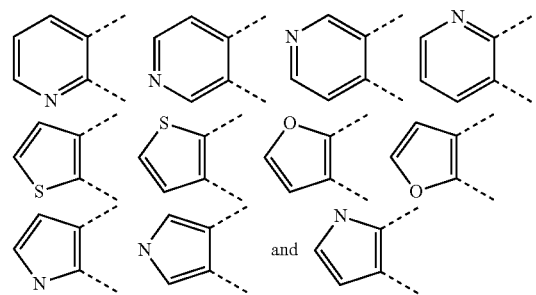

If ring A is a 5-membered heterocyclic ring it is preferred that R is bound to $G^1$ or $G^2$, in particular $G^2$, as exemplified in the following for formula (Ia):

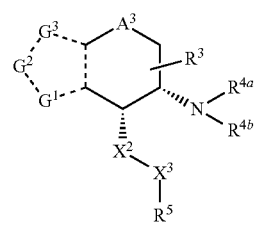

In said formula, $G^1$, $G^2$ and $G^3$ independently are —CH=, —$CH_2$—, —N=, —NH—, S or O, at least one of $G^1$, $G^2$ and $G^3$ is —CH= or —CH$_2$—, the dotted line represents a single or a double bond and $A^3$, $R^3$, $R^{4a}$, $R^{4b}$, $X^2$, $X^3$, $R^5$ are as defined herein.

If ring A is 6-membered heterocyclic ring it is preferred that R is bound to $G^1$ or $G^2$, in particular $G^2$, as exemplified in the following for formula (Ia):

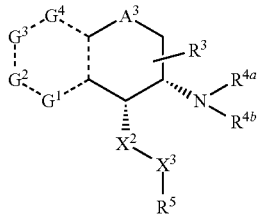

In said formula, $G^1$, $G^2$, $G^3$ and $G^4$ independently are —CH=, —CH$_2$—, —N=, —NH—, S or O, at least one of $G^1$, $G^2$, $G^3$ and $G^4$ is —CH= or —CH$_2$—, the dotted line represents a single or a double bond and $A^3$, $R^3$, $R^{4a}$, $R^{4b}$, $X^2$, $X^3$, $R^5$ are as defined herein.

Heterocyclic compounds having the following partial structures are preferred:

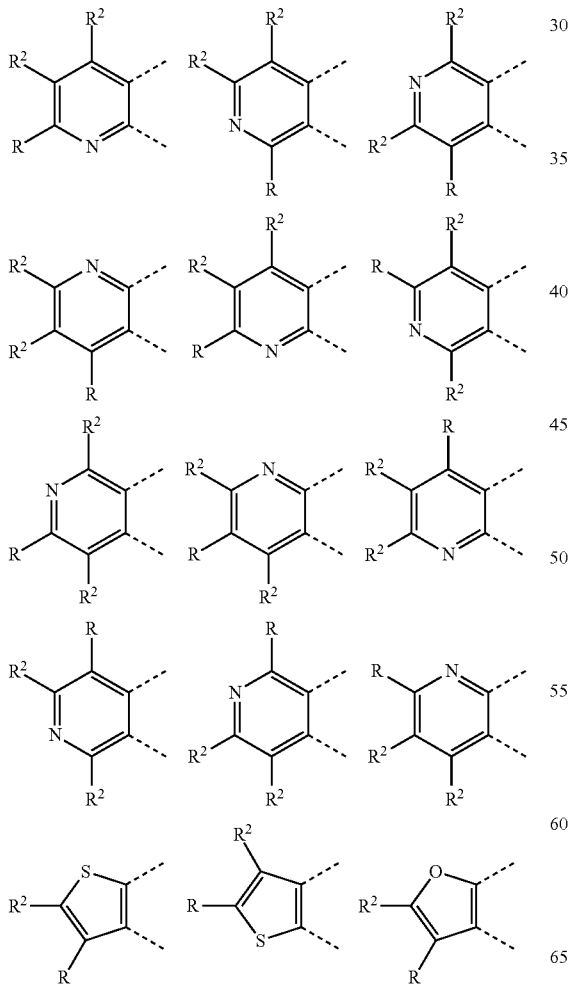

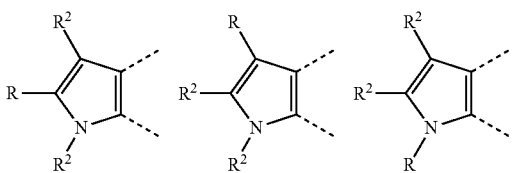

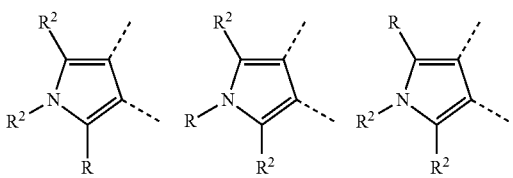

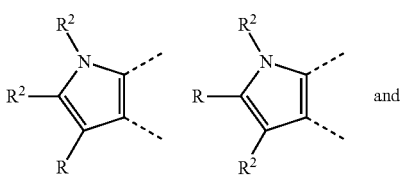

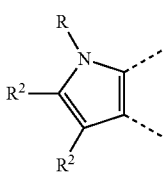 and

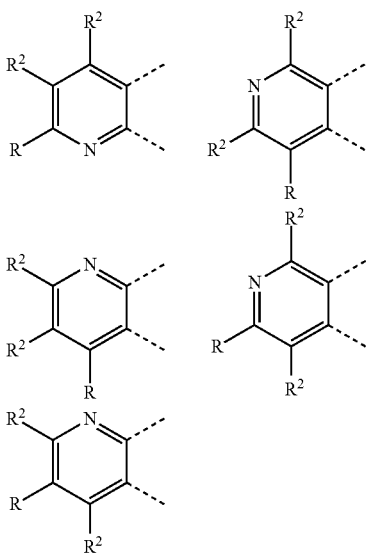

Heterocyclic compounds having the following partial structures are particularly preferred:

In said formulae, R and $R^2$ are as defined herein. If there is more than one radical $R^2$, these may be the same or different radicals.

If ring A is a benzene ring R may, in principle, be bound to the 5-, 6-, 7- or 8-position of the skeleton of the compounds of formulae (Ia), (Ib), (II), (V) and (V'). For instance, in compounds of formula (Ia) R may thus be positioned as follows:

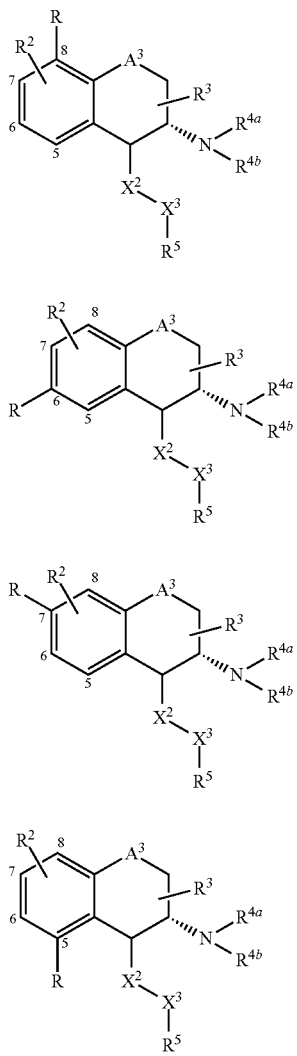

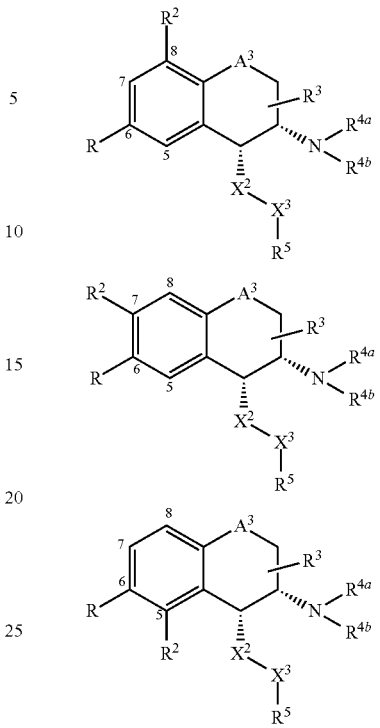

This applies accordingly to formulae (Ib), (II), (V) and (V'). It is noted that depending on the meaning of $A^3$ a different numbering may be more appropriate. However, for the sake of consistency, the indicated numbering is used for assigning positions on the core structure, irrespective of the meaning of $A^3$.

In this context those compounds of formulae (Ia), (Ib), (II), (V) and (V') with the ring A being benzene are preferred which have the radical R in the 5-, 6- or 7-position.

Particularly preferred are compounds of formulae (Ia), (Ib), (II), (V) and (V') with the ring A being benzene which have the radical R in the 6-position, i.e. R is attached in the meta position in respect to the moiety $—X^2—X^3—R^5$.

In addition to the radical R the compounds of formulae (Ia), (Ib), (II), (V) and (V') may be substituted with one or more than one radical $R^2$. If there is more than one radical $R^2$, these may be the same or different radicals. Thus, if A is benzene, the skeleton of said compounds may be substituted in 5-, 6-, 7- and/or 8-position with 1, 2 or 3 radicals $R^2$, preferably with 1 or 2 radicals $R^2$ and in particular with 1 radical $R^2$.

According to a particular embodiment, the rings A of the compounds of formulae (Ia), (Ib), (II), (V) and (V'), in case A stands for benzene, are substituted as exemplarily shown for formula (Ia) in the following:

According to a particular embodiment of the invention the variable R in the compounds of formulae (Ia), (Ib), (II) and (V) is hydrogen, halogen, —CN, or hydroxyl which optionally carries a protecting group. Suitable hydroxyl protecting groups are well known in the art such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. Suitable protecting groups in this regard include methyl, methoxymethyl, methoxyethoxymethyl, tert-butyl, allyl, 2-tetrapyranyl, benzyl, acetyl, pivaloyl, benzoyloxy, tert-butyldimethylsilyloxy and tert-butyldiphenylsilyloxy.

In the context of the preceding embodiment R in the compounds of formulae (Ia), (Ib), (II) and (V) is preferably selected from halogen, methoxy, methoxymethoxy, methoxyethoxymethoxy, tert-butyloxy, allyloxy, 2-tetrapyranyloxy, benzyloxy, acetyloxy, pivaloyloxy, benzoyloxy, tert-butyldimethylsilyloxy and tert-butyldiphenylsilyloxy, in particular from iodine, bromine, chlorine and methoxy, and specifically from bromine and methoxy.

Alternatively, the process of the invention can be carried on a bicyclic amine wherein the side chain R in the compounds of formulae (Ia), (Ib), (II) and (V) is a group $Y'-A^2-X^1—$ or a group $R^1—W-A^1-Q-Y-A^2-X^1—$ with $R^1$, W, $A^1$, Q, Y, Y', $A^2$, $X^1$ being as defined herein and in particular have one of the meanings mentioned as preferred in the following.

$R^1$ is hydrogen, $C_1-C_6$-alkyl (e.g. methyl, ethyl, n-propyl, isopropyl, n-butyl, sec-butyl or n-pentyl), $C_3-C_{12}$-cycloalkyl-$C_1-C_4$-alkyl (e.g. cyclopropylmethyl, cyclopentylmethyl or cyclohexylmethyl), halogenated $C_1-C_6$-alkyl (e.g. 3-fluoroprop-1-yl, 3-chloroprop-1-yl or 3,3,3-trifluoroprop-1-yl), tri-($C_1-C_4$-alkyl)-silyl-$C_1-C_4$-alkyl (e.g. trimethylsilylethyl), hydroxy-$C_1-C_4$-alkyl, $C_1-C_6$-alkoxy-$C_1-C_4$-alkyl (e.g. ethoxyethyl), amino-$C_1-C_4$-alkyl, $C_1-C_6$-alkylamino-$C_1-C_4$-alkyl, di-$C_1-C_6$-alkylamino-$C_1-C_4$-alkyl, $C_1-C_6$-alkylcarbonylamino-$C_1-C_4$-alkyl, $C_1-C_6$-alkyloxycarbonylamino-$C_1-C_4$-alkyl, $C_1-C_6$-alkylaminocarbonylamino-$C_1-C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 2-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1,3-dimethyl-1,2-diazol-4-yl, 1-ethyl-1,2-diazol-4-yl, 1-difluoromethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 3-pyrrolidinyl, 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl or 1-methyl-1,2,4-triazol-3-yl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

Preferably, $R^1$ is $C_1$-$C_6$-alkyl (e.g. methyl, ethyl, n-propyl, isopropyl, sec-butyl, n-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)silyl-$C_1$-$C_4$-alkyl (e.g. trimethylsilylethyl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 2-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1,3-dimethyl-1,2-diazol-4-yl, 1-ethyl-1,2-diazol-4-yl, 1-difluoromethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

In particular, $R^1$ is $C_1$-$C_6$-alkyl (e.g. n-propyl, isopropyl, 2-butyl), $C_3$-$C_{12}$-cycloalkyl-$C_1$-$C_4$-alkyl (e.g. cyclopropylmethyl), $C_3$-$C_{12}$-cycloalkyl (e.g. cyclobutyl), or optionally substituted $C_3$-$C_{12}$-heterocyclyl (e.g. 3-pyridyl, 2-pyridyl, 1-methyl-1,2-diazol-4-yl, 1,3-dimethyl-1,2-diazol-4-yl, 1-ethyl-1,2-diazol-4-yl, 1-methyl-1,3-diazol-4-yl, 3-oxetanyl, 1-methyl-pyrrol-3-yl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, furanyl, thiophenyl, piperidinyl, piperazinyl or morpholinyl, pyrrolyl, isoxazolyl and triazolyl being further examples of such $C_3$-$C_{12}$-heterocyclyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —C(O)—.

According to a particular embodiment, —W-$A^1$-Q-Y— is —W-$A^1$-$S(O)_2$—$NR^9$—, —$NR^8$—$S(O)_2$—, —$A^1$—$S(O)_2$— or —$S(O)_2$—. According to a further particular embodiment, —W-$A^1$-Q-Y— is —W-$A^1$-CO—$NR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. 1,2-ethylene or 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylene or optionally substituted $C_2$-$C_4$-alkynylene. Preferably, $A^2$ is optionally substituted $C_1$-$C_4$-alkylene (e.g. 1,2-ethylene or 1,3-propylene). More preferably, $A^2$ is $C_1$-$C_4$-alkylene (e.g. 1,2-ethylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

$X^1$ is —O—, —$NR^{11}$—, —S— or optionally substituted $C_1$-$C_4$-alkylene (e.g. —$CH_2$—, 1,2-ethylene and 1,3-propylene). In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylene or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. Preferably, $X^1$ is —O—, —$NR^{11}$—, —S—. More preferably, $X^1$ is —O—. Alternatively, it is preferred if $X^1$ is optionally substituted $C_1$-$C_4$-alkylene (e.g. —$CH_2$— or 1,2-ethylene).

According to a particular embodiment, $A^2$ is optionally substituted $C_1$-$C_4$-alkylene and $X^1$ is —O—.

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, $R^1$—W-$A^1$-Q-Y-$A^2$-$X^1$— is selected from $R^1$—S(O)$_2$—$NR^9$-$A^2$-$X^1$—, $R^1$—$NR^8$—S(O)$_2$-$A^2$-$X^1$—, $R^1$—S(O)$_2$—$X^1$—, $R^1$—C(O)—$NR^9$-$A^2$-$X^1$— and $R^1$—$NR^8$—C(O)-$A^2$-$X^1$—, preferably from $R^1$—S(O)$_2$—NH-$A^2$-$X^1$—, $R^1$—NH—S(O)$_2$-$A^2$-$X^1$—, $R^1$—S(O)$_2$—$X^1$—, $R^1$—C(O)—NH-$A^2$-$X^1$— and $R^1$—NH—C(O)-$A^2$-$X^1$—, and in particular from $R^1$—S(O)$_2$—NH-$A^2$-$X^1$— and $R^1$—S(O)$_2$—$X^1$—.

According to a particular embodiment, the structural element —Y-$A^2$-$X^1$— comprises at least 2, 3 or 4 atoms in the main chain. According to further particular embodiments the structural element —Y-$A^2$-$X^1$— has up to 4, 5 or 6 atoms in the main chain, such as 2 to 6, 2 to 5 or 2 to 4 atoms in the main chain, especially 2, 3 or 4 atoms in the main chain.

According to a further particular embodiment, —Y-$A^2$-$X^1$— is —$C_1$-$C_4$-alkylene-O— or —$NR^9$—$C_1$-$C_4$-alkylene-O—, with —Y-$A^2$-$X^1$— preferably having 2 to 6, 3 to 5 and especially 4 atoms in the main chain. Particular examples of —Y-$A^2$-$X^1$— include —(CH$_2$)$_3$—O— and —$NR^9$—(CH$_2$)$_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_1$-$C_4$-alkylene- (e.g. —NH—$CH_2$—, —NH—(CH$_2$)$_2$— or —NH—(CH$_2$)$_3$—), with —Y-$A^2$-$X^1$— preferably having 2 to 6, 2 to 5, 2 to 4 and especially 2, 3 or 4 atoms in the main chain. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl); or $R^9$ is $C_1$-$C_4$-alkylene that is bound to a carbon atom in $X^1$ which is $C_1$-$C_4$-alkylene.

According to a further particular embodiment, —Y-$A^2$-$X^1$— is —$NR^9$—$C_2$-$C_4$-alkenylene- or —$NR^9$—$C_2$-$C_4$-alkynylene- (e.g. —NH—$CH_2$—C≡C—), with —Y-$A^2$-$X^1$— preferably having 2 to 6, 3 to 5 and especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl). If A is a heterocyclic ring, this embodiment of —Y-$A^2$-$X^1$— is particularly suitable.

According to a further particular embodiment, —Y-$A^2$-$X^1$— is —$C_1$-$C_4$-alkylene- (e.g. —(CH$_2$)$_2$—), with —Y-$A^2$-$X^1$— preferably having 2 to 6, 2 to 5, 2 to 4 and especially 2 atoms in the main chain. If A is a heterocyclic ring, this embodiment of —Y-$A^2$-$X^1$— is particularly suitable.

According to a further particular embodiment, the structural motif —Y-$A^2$-$X^1$ as disclosed herein is bound to Q being —S(O)$_2$— or —C(O)—. Particular examples for this embodiment include heterocyclic compounds of the invention wherein R is $R^1$—S(O)$_2$—Y-$A^2$-$X^1$ or $R^1$—C(O)—Y-$A^2$-$X^1$.

Y' is Y or Y which carries a protecting group. In case Y' is $NR^9$ the protecting group is an amino protecting group which can be chosen from the amino protecting groups well known in the art that are described, for example, in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. Particularly useful amino protecting groups here are optionally substituted alkylcarbonyl (e.g., tert-butylcarbonyl), optionally substituted arylcarbonyl, optionally substituted arylalkycarbonyl (e.g., benzylcarbonyl), optionally substituted alkoxycarbonyl (e.g., methoxycarbonyl or tert-butyloxycarbonyl), optionally substituted aryloxycarbonyl (e.g. phenoxycarbonyl) or optionally substituted arylalkoxycarbonyl (e.g. benzyloxycarbonyl).

The radical $R^2$ in the compounds of formulae (Ia), (Ib), (II), (V) and (V') is hydrogen, halogen (e.g. fluorine), $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms to which they are bound form a 5- or 6 membered ring.

An 5- or 6-membered ring that is formed by two radicals $R^2$ together with the ring atoms of A to which they are bound is, for instance, a benzene ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen (e.g. fluorine) or $C_1$-$C_6$-alkoxy. In particular, $R^2$ is hydrogen or halogen (e.g. fluorine).

The variable $A^3$ in the compounds of formulae (Ia), (Ib), (II), (V) and (V') is —O—, —S—, —NR$^{16}$—, a bond or $C_1$-$C_2$-alkylene. According to a preferred embodiment, $A^3$ is —O— or —CH$_2$—.

The compounds of formulae (Ia), (Ib), (II), (V) and (V') may be substituted in the 2-, 3- and/or 4-positions, with one or more than one radical $R^3$. If there is more than one radical $R^3$, these may be the same or different radicals. The compounds of formula (Ia), for instance, may therefore be represented by the following formula:

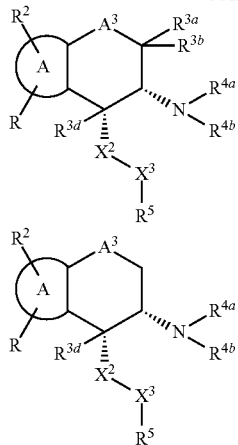

wherein $R^{3a}$, $R^{3b}$, $R^{3c}$, $R^{3d}$ independently have one of the meanings given for $R^3$, and A, R, $R^2$, $A^3$, $R^{4a}$, $R^{4b}$, $X^2$, $X^3$, $R^5$ are as defined herein. Again, it is noted that depending on the meaning of $A^3$ a different numbering may be more appropriate. However, for the sake of consistency, the indicated numbering is used for assigning positions on the core structure, irrespective of the meaning of $A^3$.

According to a particular embodiment, the compounds of formula (Ia), and accordingly the compounds of formulae (Ib), (II), (V) and (V'), have one of the following formulae:

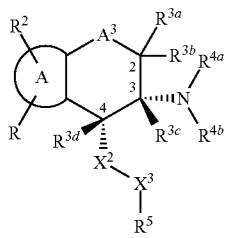

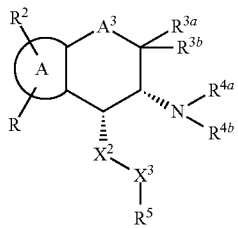

wherein $R^{3a}$, $R^{3b}$, $R^{3d}$ independently have the meaning of $R^3$ and A, R, $R^2$, $A^3$, $R^3$, $R^{4a}$, $R^{4b}$, $X^2$, $X^3$, $R^5$ are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl (e.g. methyl). In particular, $R^3$ is hydrogen.

The radical $R^{4a}$ in the compounds of formulae (Ia), (Ib) and (II) is $C_1$-$C_4$-alkylcarbonyl (e.g. methylcarbonyl, ethylcarbonyl or isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl or 1,1,1-trifluoroprop-3-ylcarbonyl) or $C_6$-$C_{12}$-arylcarbonyl (e.g. phenylcarbonyl).

Preferably, $R^{4a}$ in the compounds of formulae (Ia), (Ib) and (II) is $C_1$-$C_4$-alkylcarbonyl (e.g. methylcarbonyl, ethylcarbonyl or isopropylcarbonyl) or (halogenated $C_1$-$C_4$-alkyl)carbonyl (e.g. fluoromethylcarbonyl, difluoromethylcarbonyl, trifluoromethylcarbonyl or 1,1,1-trifluoroeth-2-ylcarbonyl).

The radical $R^{4b}$ in the compounds of formulae (Ia), (Ib) and (II) is hydrogen or $C_1$-$C_6$-alkyl (e.g. methyl, ethyl), and preferably hydrogen.

According to particular embodiment of the present invention in the compounds of formulae (Ia), (Ib) and (II) the radical $R^{4a}$ is $C_1$-$C_4$-alkylcarbonyl, preferably propylcarbonyl, and the radical $R^{4b}$ is hydrogen.

Alternatively, $R^{4a}$, $R^{4b}$ in the compounds of formulae (Ia), (Ib) and (II) are together $C_2$-$C_{10}$-alkylenecarbonyl, preferably $C_2$-$C_6$-alkylenecarbonyl and in particular $C_2$-$C_4$-alkylenecarbonyl (e.g. 2-ethylenecarbonyl, 3-propylenecarbonyl, 2-propylenecarbonyl, 4-butylenecarbonyl or 3-butylenecarbonyl).

According to another particular embodiment of the present invention in the compounds of formulae (Ia), (Ib) and (II) the radical $R^{4a}$ and $R^{4b}$ are together 2-ethylenecarbonyl, 3-propylenecarbonyl or 4-butylenecarbonyl, i.e. $R^{4a}$ and $R^{4b}$ in combination with the N-atom to which they are bond form an azetidin-2-onyl, a pyrrolidin-2-onyl or a piperidin-2-onyl moiety.

The radical $X^2$ in the compounds of formulae (Ia), (Ib), (II), (V) and (V') is —O—, —NR$^6$—, —S—, >CR$^{12a}$R$^{12b}$ or a bond. Preferably, $X^2$ is >CR$^{12a}$R$^{12b}$.

The radical $X^3$ in the compounds of formulae (Ia), (Ib), (II), (V) and (V') is —O—, —NR$^7$—, —S—, >CR$^{13a}$R$^{13b}$ or a bond. Preferably, $X^3$ is a bond.

Thus, it is preferred that $X^2$ is >CR$^{12a}$R$^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl, and in particular is hydrogen.

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl, and in particular is hydrogen.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are carbonyl or, preferably, optionally substituted $C_1$-$C_4$-alkylene (e.g. 1,3-propylene), wherein one —$CH_2$— of $C_1$-$C_4$-alkylene may be replaced by an oxygen atom or —$NR^{14}$—/—$NR^{15}$—.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted $C_1$-$C_4$-alkylene (e.g. 1,3-propylene), or $R^{13a}$ and $R^{13b}$ together are optionally substituted $C_1$-$C_4$-alkylene (e.g. 1,3-propylene).

The radical $R^5$ in the compounds of formulae (Ia), (Ib), (II), (V) and (V') is optionally substituted $C_6$-$C_{12}$-aryl (e.g. phenyl, 2-fluorophenyl, 2-chlorophenyl, 3-fluorophenyl, 3-chlorophenyl; 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 2,4-dichlorophenyl or 3,4-dichlorophenyl), optionally substituted $C_3$-$C_{12}$-cycloalkyl (e.g. cyclohexyl) or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, and in particular has the formula (VI):

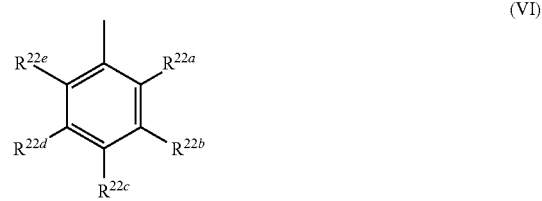

(VI)

wherein $R^{22a}$, $R^{22b}$, $R^{22c}$, $R^{22d}$ and $R^{22e}$, independently of each other, are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

It is also preferred that $R^5$ is optionally substituted $C_6$-$C_{12}$-hetaryl, and in particular has the formula (VII):

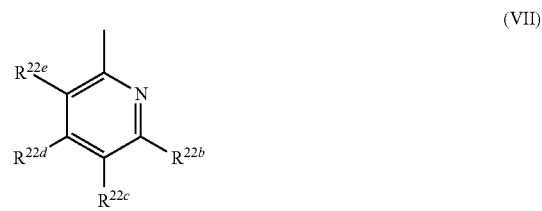

(VII)

wherein $R^{22b}$, $R^{22c}$, $R^{22d}$ and $R^{22e}$, independently of each other, are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

In connection with $R^5$ or $R^{22a}$, $R^{22b}$, $R^{22c}$, $R^{22d}$, $R^{22e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment $R^{22a}$, if present, $R^{22b}$, $R^{22c}$, $R^{22d}$ and $R^{22e}$ are all hydrogen.

According to a further particular embodiment $R^{22a}$, if present, $R^{22b}$, $R^{22d}$ and $R^{22e}$ are hydrogen and $R^{22c}$ is different from hydrogen (para-mono-substitution).

According to a further particular embodiment $R^{22a}$, if present, $R^{22c}$, $R^{22d}$ and $R^{22e}$ are hydrogen and $R^{22b}$ is different from hydrogen (meta-mono-substitution).

In connection with $R^{22a}$, $R^{22b}$, $R^{22c}$, $R^{22d}$ and $R^{22e}$, $C_3$-$C_{12}$-heterocyclyl in particular includes morpholinyl, imidazolyl and pyrazolyl.

$R^6$ is hydrogen or $C_1$-$C_6$-alkyl. Preferably, $R^6$ is hydrogen.
$R^7$ is hydrogen or $C_1$-$C_6$-alkyl. Preferably, $R^7$ is hydrogen.
$R^8$ is hydrogen or $C_1$-$C_6$-alkyl. Preferably, $R^8$ is hydrogen.

$R^9$ is hydrogen, $C_1$-$C_6$-alkyl (e.g. methyl or ethyl), $C_3$-$C_{12}$-cycloalkyl (e.g. cyclopropyl), amino-$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl (e.g. methyl or ethyl).

According to a particular embodiment, $R^9$ and $R^1$ together are $C_1$-$C_4$-alkylene (e.g. 1,3-1,2-ethylene or propylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

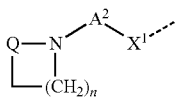

wherein Q, $A^2$, $X^1$, are as defined herein (e.g. $S(O)_2$) and n is 0, 1, 2, 3 or 4.

According to a further particular embodiment, $R^9$ is $C_1$-$C_4$-alkylene (e.g. methylene or 1,3-propylene) that is bound to a carbon atom in $A^2$ and $A^2$ is $C_1$-$C_4$-alkylene so that $R^9$ and at least part of $A^2$ together with the nitrogen atom to which $R^9$ is bound form an N-containing heterocyclic ring having, in particular, 4, 5, 6 or 7 ring member atoms (including the nitrogen atom). Such a ring may be represented by the following partial structure:

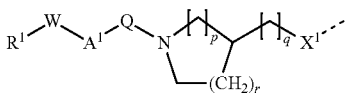

wherein $R^1$, W, $A^1$, Q and $X^1$ are as defined herein, p is 1 or 2, r is 0, 1 or 2 and q is 0, 1 or 2. In this particular embodiment, $X^1$ preferably is —O—. Particular combinations of p, r and q include p=1, r=0, q=1; and p=1, r=0, q=0. Alternatively, p is 0, r is 3 and q is 1, with $X^1$ preferably being —O—.

According to a further particular embodiment, $R^9$ is $C_1$-$C_4$-alkylene (e.g. methylene or 1,3-propylene) that is bound to a carbon atom in $X^1$ and $X^1$ is $C_1$-$C_4$-alkylene (e.g. 1,2-ethylene) so that $R^9$ and at least part of $X^1$ together with the nitrogen atom to which $R^9$ is bound form an N-containing heterocyclic ring having, in particular, 4, 5, 6 or 7 ring member atoms (including the nitrogen atom). With $A^2$ being a bond, such a ring may be represented by the following partial structure:

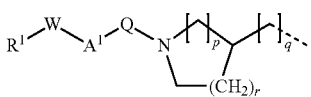

wherein $R^1$, W, $A^1$ and Q are as defined herein, p is 1 or 2, r is 0, 1 or 2 and q is 0, 1 or 2. Particular combinations of p, r and q include p=1, r=0, q=0.

$R^{10}$ is hydrogen, $C_1$-$C_6$-alkyl or $C_1$-$C_6$-alkylsulfonyl. Preferably, $R^{10}$ is hydrogen.

$R^{11}$ is hydrogen or $C_1$-$C_6$-alkyl. Preferably, $R^{11}$ is hydrogen.

Alternatively, $R^9$, $R^{11}$ together are $C_1$-$C_4$-alkylene (e.g. ethylene).

$R^{14}$ is hydrogen or $C_1$-$C_6$-alkyl. Preferably, $R^{14}$ is hydrogen.

$R^{15}$ is hydrogen or $C_1$-$C_6$-alkyl. Preferably, $R^{15}$ is hydrogen.

$R^{16}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl. Preferably, $R^{16}$ is hydrogen.

Particular embodiments of the invention result if
A is a benzene ring;
R is hydrogen, halogen, —CN, or hydroxyl which optionally carries a protecting group;
$R^2$ is hydrogen or halogen (e.g. fluorine);
$A^3$ is —CH$_2$—;
$R^3$ is hydrogen or $C_1$-$C_6$-alkyl (e.g. methyl);
$R^{4a}$ is $C_1$-$C_4$-alkylcarbonyl (e.g. ethylcarbonyl), (halogenated $C_1$-$C_4$-alkyl)carbonyl or $C_6$-$C_{12}$-arylcarbonyl;
$R^{4b}$ is hydrogen; or
$R^{4a}$, $R^{4b}$
together are $C_2$-$C_{10}$-alkylenecarbonyl (e.g. 2-ethylenecarbonyl, 3-propylenecarbonyl or 4-butylenecarbonyl);
$X^2$ is >CR$^{12a}$R$^{12b}$;
$X^3$ is a bond;
$R^5$ is optionally substituted phenyl (e.g. phenyl, 2-fluorophenyl, 2-chlorophenyl, 3-fluorophenyl, 3-chlorophenyl, 3-trifluoromethylphenyl);
$R^{12a}$ is hydrogen or $C_1$-$C_6$-alkyl;
$R^{12b}$ is hydrogen; or
$R^{12a}$, $R^{12b}$
together are $C_1$-$C_4$-alkylene (e.g. 1,3-propylene).

Further particular embodiments of the present invention are the processes for preparing a bicyclic amine derivative of the formula (Ic) or (Id) as listed in the following tables 1 to 24:

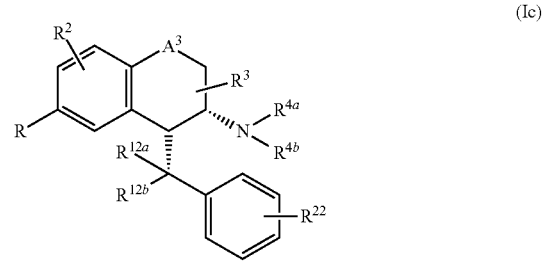

(Ic)

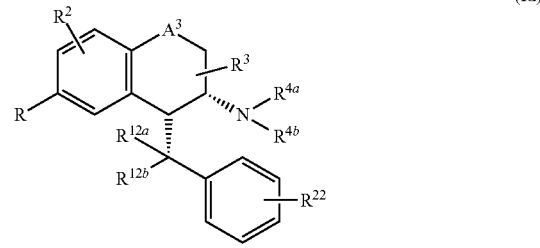

(Id)

Table 1

Derivatives of the formula (Ic) or (Id) wherein R is as defined herein and in particular represents Br or methoxy; $R^2$ is hydrogen, $R^3$ is as defined herein and in particular represents hydrogen, $R^{22}$ is hydrogen and the combination of $A^3$, $>CR^{12a}R^{12b}$, $R^{4a}$, $R^{4b}$ for a derivatives in each case corresponds to one line of Table A (A-1 to A-24).

Table 2
Derivatives of the formula (Ic) or (Id) wherein R is as defined herein and in particular represents Br or methoxy; $R^2$ is hydrogen, $R^3$ is as defined herein and in particular represents hydrogen, $R^{22}$ is 3-F and the combination of $A^3$, $>CR^{12a}R^{12b}$, $R^{4a}$, $R^{4b}$ for a derivatives in each case corresponds to one line of Table A (A-1 to A-24).

Table 3
Derivatives of the formula (Ic) or (Id) wherein R is as defined herein and in particular represents Br or methoxy; $R^2$ is hydrogen, $R^3$ is as defined herein and in particular represents hydrogen, $R^{22}$ is 3-Cl and the combination of $A^3$, $>CR^{12a}R^{12b}$, $R^{4a}$, $R^{4b}$ for a derivatives in each case corresponds to one line of Table A (A-1 to A-24).

Table 4
Derivatives of the formula (Ic) or (Id) wherein R is as defined herein and in particular represents Br or methoxy; $R^2$ is hydrogen, $R^3$ is as defined herein and in particular represents hydrogen, $R^{22}$ is 3-$CF_3$ and the combination of $A^3$, $>CR^{12a}R^{12b}$, $R^{4a}$, $R^{4b}$ for a derivatives in each case corresponds to one line of Table A (A-1 to A-24).

Table 5
Derivatives of the formula (Ic) or (Id) wherein R is as defined herein and in particular represents Br or methoxy; $R^2$ is hydrogen, $R^3$ is as defined herein and in particular represents hydrogen, $R^{22}$ is 4-F and the combination of $A^3$, $>CR^{12a}R^{12b}$, $R^{4a}$, $R^{4b}$ for a derivatives in each case corresponds to one line of Table A (A-1 to A-24).

Table 6
Derivatives of the formula (Ic) or (Id) wherein R is as defined herein and in particular represents Br or methoxy; $R^2$ is hydrogen, $R^3$ is as defined herein and in particular represents hydrogen, $R^{22}$ is 4-Cl and the combination of $A^3$, $>CR^{12a}R^{12b}$, $R^{4a}$, $R^{4b}$ for a derivatives in each case corresponds to one line of Table A (A-1 to A-24).

Table 7
Derivatives of the formula (Ic) or (Id) wherein R is as defined herein and in particular represents Br or methoxy; $R^2$ is 5-F, $R^3$ is as defined herein and in particular represents hydrogen, $R^{22}$ is hydrogen and the combination of $A^3$, $>CR^{12a}R^{12b}$, $R^{4a}$, $R^{4b}$ for a derivatives in each case corresponds to one line of Table A (A-1 to A-24).

Table 8
Derivatives of the formula (Ic) or (Id) wherein R is as defined herein and in particular represents Br or methoxy; $R^2$ is 5-F, $R^3$ is as defined herein and in particular represents hydrogen, $R^{22}$ is 3-F and the combination of $A^3$, $>CR^{12a}R^{12b}$, $R^{4a}$, $R^{4b}$ for a derivatives in each case corresponds to one line of Table A (A-1 to A-24).

Table 9
Derivatives of the formula (Ic) or (Id) wherein R is as defined herein and in particular represents Br or methoxy; $R^2$ is 5-F, $R^3$ is as defined herein and in particular represents hydrogen, $R^{22}$ is 3-Cl and the combination of $A^3$, $>CR^{12a}R^{12b}$, $R^{4a}$, $R^{4b}$ for a derivatives in each case corresponds to one line of Table A (A-1 to A-24).

Table 10
Derivatives of the formula (Ic) or (Id) wherein R is as defined herein and in particular represents Br or methoxy; $R^2$ is 5-F, $R^3$ is as defined herein and in particular represents hydrogen, $R^{22}$ is 3-$CF_3$ and the combination of $A^3$, $>CR^{12a}R^{12b}$, $R^{4a}$, $R^{4b}$ for a derivatives in each case corresponds to one line of Table A (A-1 to A-24).

Table 11
Derivatives of the formula (Ic) or (Id) wherein R is as defined herein and in particular represents Br or methoxy; $R^2$ is 5-F, $R^3$ is as defined herein and in particular represents hydrogen, $R^{22}$ is 4-F and the combination of $A^3$, $>CR^{12a}R^{12b}$, $R^{4a}$, $R^{4b}$ for a derivatives in each case corresponds to one line of Table A (A-1 to A-24).

Table 12
Derivatives of the formula (Ic) or (Id) wherein R is as defined herein and in particular represents Br or methoxy; $R^2$ is 5-F, $R^3$ is as defined herein and in particular represents hydrogen, $R^{22}$ is 4-Cl and the combination of $A^3$, $>CR^{12a}R^{12b}R^{4a}$, $R^{4b}$ for a derivatives in each case corresponds to one line of Table A (A-1 to A-24).

Table 13
Derivatives of the formula (Ic) or (Id) wherein R is as defined herein and in particular represents Br or methoxy; $R^2$ is 7-F, $R^3$ is as defined herein and in particular represents hydrogen, $R^{22}$ is hydrogen and the combination of $A^3$, $>CR^{12a}R^{12b}$, $R^{4a}$, $R^{4b}$ for a derivatives in each case corresponds to one line of Table A (A-1 to A-24).

Table 14
Derivatives of the formula (Ic) or (Id) wherein R is as defined herein and in particular represents Br or methoxy; $R^2$ is 7-F, $R^3$ is as defined herein and in particular represents hydrogen, $R^{22}$ is 3-F and the combination of $A^3$, $>CR^{12a}R^{12b}$, $R^{4a}$, $R^{4b}$ for a derivatives in each case corresponds to one line of Table A (A-1 to A-24).

Table 15
Derivatives of the formula (Ic) or (Id) wherein R is as defined herein and in particular represents Br or methoxy; $R^2$ is 7-F, $R^3$ is as defined herein and in particular represents hydrogen, $R^{22}$ is 3-Cl and the combination of $A^3$, $>CR^{12a}R^{12b}$, $R^{4a}$, $R^{4b}$ for a derivatives in each case corresponds to one line of Table A (A-1 to A-24).

Table 16
Derivatives of the formula (Ic) or (Id) wherein R is as defined herein and in particular represents Br or methoxy; $R^2$ is 7-F, $R^3$ is as defined herein and in particular represents hydrogen, $R^{22}$ is 3-$CF_3$ and the combination of $A^3$, $>CR^{12a}R^{12b}$, $R^{4a}$, $R^{4b}$ for a derivatives in each case corresponds to one line of Table A (A-1 to A-24).

Table 17
Derivatives of the formula (Ic) or (Id) wherein R is as defined herein and in particular represents Br or methoxy; $R^2$ is 7-F, $R^3$ is as defined herein and in particular represents hydrogen, $R^{22}$ is 4-F and the combination of $A^3$, $>CR^{12a}R^{12b}$, $R^{4a}$, $R^{4b}$ for a derivatives in each case corresponds to one line of Table A (A-1 to A-24).

Table 18
Derivatives of the formula (Ic) or (Id) wherein R is as defined herein and in particular represents Br or methoxy; $R^2$ is 7-F, $R^3$ is as defined herein and in particular represents hydrogen, $R^{22}$ is 4-Cl and the combination of $A^3$, $>CR^{12a}R^{12b}$, $R^{4a}$, $R^{4b}$ for a derivatives in each case corresponds to one line of Table A (A-1 to A-24).

Table 19 Derivatives of the formula (Ic) or (Id) wherein R is as defined herein and in particular represents Br or methoxy; $R^2$ is 8-F, $R^3$ is as defined herein and in particular represents hydrogen, $R^{22}$ is hydrogen and the combination of $A^3$, $>CR^{12a}R^{12b}$, $R^{4a}$, $R^{4b}$ for a derivatives in each case corresponds to one line of Table A (A-1 to A-24).

Table 20
Derivatives of the formula (Ic) or (Id) wherein R is as defined herein and in particular represents Br or methoxy; $R^2$ is 8-F, $R^3$ is as defined herein and in particular represents hydrogen, $R^{22}$ is 3-F and the combination of $A^3$, $>CR^{12a}R^{12b}$, $R^{4a}$, $R_{4b}$ for a derivatives in each case corresponds to one line of Table A (A-1 to A-24).

Table 21

Derivatives of the formula (Ic) or (Id) wherein R is as defined herein and in particular represents Br or methoxy; $R^2$ is 8-F, $R^3$ is as defined herein and in particular represents hydrogen, $R^{22}$ is 3-Cl and the combination of $A^3$, $>CR^{12a}R^{12b}$, $R^{4a}$, $R^{4b}$ for a derivatives in each case corresponds to one line of Table A (A-1 to A-24).

Table 22

Derivatives of the formula (Ic) or (Id) wherein R is as defined herein and in particular represents Br or methoxy; $R^2$ is 8-F, $R^3$ is as defined herein and in particular represents hydrogen, $R^{22}$ is 3-CF$_3$ and the combination of $A^3$, $>CR^{12a}R^{12b}$, $R^{4a}$, $R^{4b}$ for a derivatives in each case corresponds to one line of Table A (A-1 to A-24).

Table 23

Derivatives of the formula (Ic) or (Id) wherein R is as defined herein and in particular represents Br or methoxy; $R^2$ is 8-F, $R^3$ is as defined herein and in particular represents hydrogen, $R^{22}$ is 4-F and the combination of $A^3$, $>CR^{12a}R^{12b}$, $R^{4a}$, $R_{4b}$ for a derivatives in each case corresponds to one line of Table A (A-1 to A-24).

Table 24

Derivatives of the formula (Ic) or (Id) wherein R is as defined herein and in particular represents Br or methoxy; $R^2$ is 8-F, $R^3$ is as defined herein and in particular represents hydrogen, $R^{22}$ is 4-Cl and the combination of $A^3$, $>CR^{12a}R^{12b}$, $R^{4a}$, $R_{4b}$ for a derivatives in each case corresponds to one line of Table A (A-1 to A-24).

| | $A^3$ | $>CR^{12a}R^{12b}$ | $R^{4a}$, $R^{4b}$ |
|---|---|---|---|
| A-1. | —CH$_2$— | —CH$_2$— | methylcarbonyl, H |
| A-2. | —O— | —CH$_2$— | methylcarbonyl, H |
| A-3. | bond | —CH$_2$— | methylcarbonyl, H |
| A-4. | —CH$_2$— | 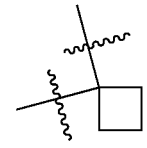 [SMILES: *C1(*)CCC1] | methylcarbonyl, H |
| A-5. | —O— | 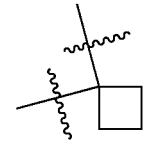 [SMILES: *C1(*)CCC1] | methylcarbonyl, H |
| A-6. | bond | 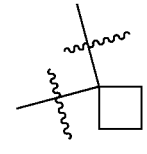 [SMILES: *C1(*)CCC1] | methylcarbonyl, H |
| A-7. | —CH$_2$— | —CH$_2$— | ethylcarbonyl, H |
| A-8. | —O— | —CH$_2$— | ethylcarbonyl, H |
| A-9. | bond | —CH$_2$— | ethylcarbonyl, H |
| A-10. | —CH$_2$— | 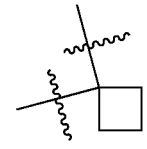 [SMILES: *C1(*)CCC1] | ethylcarbonyl, H |
| A-11. | —O— | 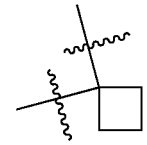 [SMILES: *C1(*)CCC1] | ethylcarbonyl, H |
| A-12. | bond | 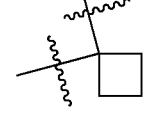 | ethylcarbonyl, H |
| A-13. | —CH2— | —CH2— | —(CH$_2$)$_3$—CO— |
| A-14. | —O— | —CH2— | —(CH$_2$)$_3$—CO— |
| A-15. | bond | —CH2— | —(CH$_2$)$_3$—CO— |
| A-16. | —CH2— | 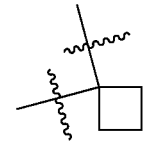 [SMILES: *C1(*)CCC1] | —(CH$_2$)$_3$—CO— |
| A-17. | —O— | 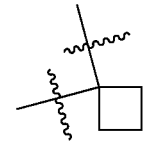 [SMILES: *C1(*)CCC1] | —(CH$_2$)$_3$—CO— |
| A-18. | bond | 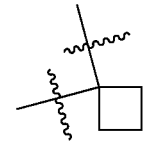 [SMILES: *C1(*)CCC1] | —(CH$_2$)$_3$—CO— |
| A-19. | —CH2— | —CH2— | —(CH$_2$)$_4$—CO— |
| A-20. | —O— | —CH2— | —(CH$_2$)$_4$—CO— |
| A-21. | bond | —CH2— | —(CH$_2$)$_4$—CO— |
| A-22. | —CH2— | 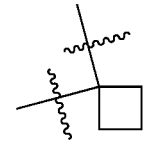 [SMILES: *C1(*)CCC1] | —(CH$_2$)$_4$—CO— |
| A-23. | —O— | 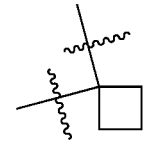 [SMILES: *C1(*)CCC1] | —(CH$_2$)$_4$—CO— |
| A-24. | bond | 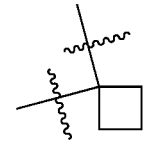 [SMILES: *C1(*)CCC1] | —(CH$_2$)$_4$—CO— |

The invention is further illustrated by the following non-limiting examples.

EXAMPLES

Hereinafter, the following abbreviations are used:
aq.=aqueous
% ee=enantiomeric excess
r.t.=room temperature
CDI=corona discharge ionisation
THF=tetrahydrofuran
IPA=isopropanol
MeOH=methanol
ACN=acetonitrile
EtOH=ethanol
MTBE=methyl tert-butyl ether
EtOAc=ethyl acetate The ligand Josiphos SL-J216-2 (Solvias AG, Basel, Switzerland) used in Examples 3 to 7 below is a chiral diphosphine ligand of the formula (IVa) with the radicals $R^{18}$ and $R^{19}$ both being tert-butyl and the radicals $R^{20}$ and $R^{21}$ both being 1-naphthyl.

The following analytical procedures were employed:

HPLC chiral analyses: Agilent 1100 HPLC using a Daicel Chiralpak AD-H column (4.6 mm×250 mm). Elution: 0.50 ml/min flow rate, 10% MeOH+10% EtOH in hexanes, at 40° C. over 25 min, monitored at 220 nm.

Approximately 1 mg of analyte in 1 mL of mobile phase was injected for each analysis.

Reverse-phase HPLC analyses: Agilent Zorbax RX-C8 column (5 µm, 4.6×150 mm), monitored at 210 nm. Elution: 1.5 ml/min flow rate, gradient using 0.1% aq. phosphoric acid and acetonitrile, with a gradient profile of
0 min: 60% ACN+40% 0.1% aq. phosphoric acid,
13 min: 80% ACN+20% 0.1% aq. phosphoric acid,
20 min: 80% ACN+20% 0.1% aq. phosphoric acid.

MS-method: CDI positive $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singlett.

I. Preparation of a Ketone of the General Formula (V)

Example 1a

1-Benzyl-7-bromo-3,4-dihydronaphthalen-2(1H)-one

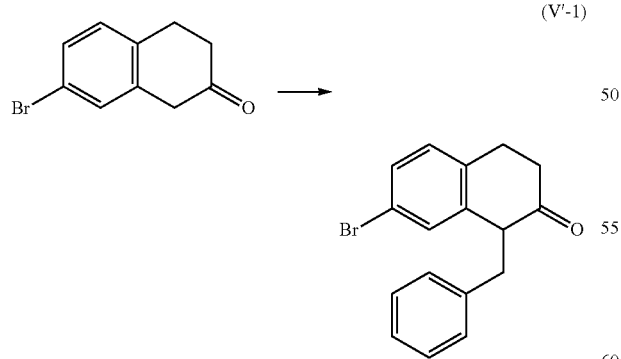

(V'-1)

In a flask were charged 7-bromo-3,4-dihydronaphthalen-2(1H)-one (20.26 g, 90 mmol) and (150 ml) under nitrogen. The solution was cooled to 5° C. and a MeOH solution of pyrrolidine (11.16 ml, 135 mmol in 10 ml of MeOH) was added slowly keeping the temperature below 15° C. The resulting yellow colored suspension was stirred at room temperature for 4 hours and monitored by HPLC until starting material is less than 10%). The suspension was cooled to 0° C. and stirred at 0° C. for 30 min, and then filtered. The white enamine intermediate (24.5 g) was air dried for 2 hours and the major portion (24.15 g) was charged to a flask followed by addition of $CH_3CN$ (250 ml) to give a suspension. To the suspension was then added benzyl bromide (11.77 ml, 99 mmol). The resulting reaction mixture was stirred at r.t. overnight. To the suspension was added 200 ml MTBE and cooled to 0° C. for 2 hrs. The resulting suspension was filtered and air dried to give a white solid (34.06 g). The major portion of the white solid (33.85 g) was charged to a flask followed by MeOH (150 ml), water (150 ml) and acetic acid (20 ml). A clear solution formed and the mixture was stirred at r.t. overnight. The mixture became cloudy and was monitored by HPLC which indicated that the starting material was completely consumed.

The reaction mixture was extracted with MTBE (3×200 ml), the combined organic layers were washed with 5% $NaHCO_3$ (2×200 ml) and brine (200 ml), dried over $Na_2SO_4$ and concentrated under vacuum to give a light yellow thick oil which was further dried under high vacuum to give 25.0 g product as a light colored thick oil. The product was used in the next step without further purification.

MS data: $C_{17}H_{15}BrO$, MW 315.2, $[M+NH_4]^+$=332.

$^1$H NMR data: (400 MHz, $CDCL_3$) δ 7.32-7.26 (m, 1H), 7.18-7.14 (m, 3H), 7.02 (dd, J=30.1, 5.0 Hz, 2H), 6.88-6.82 (m, 2H), 3.71-3.62 (m, 1H), 3.27-3.10 (m, 2H), 2.79-2.70 (m, 1H), 2.54-2.35 (m, 3H).

Example 1b

1-Benzyl-7-methoxy-3,4-dihydronaphthalen-2(1H)-one

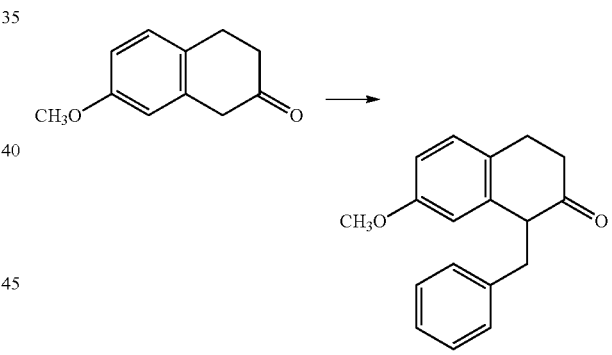

In a flask were charged 7-methoxy-3,4-dihydronaphthalen-2(1H)-one (50 g, 284 mmol) and THF (500 ml) under nitrogen. Pyrrolidine (23.47 ml, 284 mmol) was added in one portion. The resulting yellow colored solution was heated to reflux and distilled to about 250 ml at atmospheric pressure. Distillation was continued while adding acetonitrile (500 ml), at a rate such that the volume in the reaction flask was maintained at 250 ml. The solution was cooled to 70° C. and benzyl bromide (37.1 ml, 312 mmol) was added, leading to a temperature increase to 82° C. The resulting reaction mixture was refluxed at 82° C. for 2 hrs. The solution was cooled to 45° C. and MTBE (750 ml) was added over 15 minutes. The resulting suspension was cooled to room temperature over 1 hr, then cooled to 0° C., filtered and dried to give a white solid (100.5 g). The major portion of the white solid (75 g, 187 mmol) was charged to a flask followed by toluene (750 ml), water (750 ml) and acetic acid (21.45 ml). The mixture was heated to 35° C. and mixed for 20 hr under nitrogen. The reaction mixture was monitored by HPLC which indicated that that the starting material was completely consumed.

The reaction mixture cooled to r.t. and layers were separated, the organic layer was washed with water (250 ml) and organics were concentrated to near dryness and chased with toluene (2×100 ml) and heptane (3×100 ml). The resulting orange oil was diluted with heptane (300 ml) and heated to 85° C. The oil dissolved to give a light yellow/orange solution. The solution was stirred and allowed to cool to r.t. The solids formed on cooling and suspension was cooled to 0° C. The solids were filtered and washed with heptane (50 ml). Solids were dried under vacuum to give 44.2 g (yield: 89%) product as a white solid.

MS data: $C_{18}H_{18}O_2$, MW 266.3, $[M+NH_4]^+=283$.

$^1$H NMR data: (400 MHz, $CDCL_3$) δ 7.30-7.26 (m, 1H), 7.16-7.14 (m, 3H), 6.84-6.90 (m, 2H), 6.65 (d, 1H), 6.40 (s, 1H), 3.85 (s, 3H), 3.85-3.80 (m, 1H), 3.26-3.15 (m, 2H), 2.80-2.76 (m, 1H), 2.60-2.38 (m, 3H).

II. Preparation of an Enamine of the General Formula (II)

Example 2a

N-(1-benzyl-7-bromo-3,4-dihydronaphthalen-2-yl)propionamide

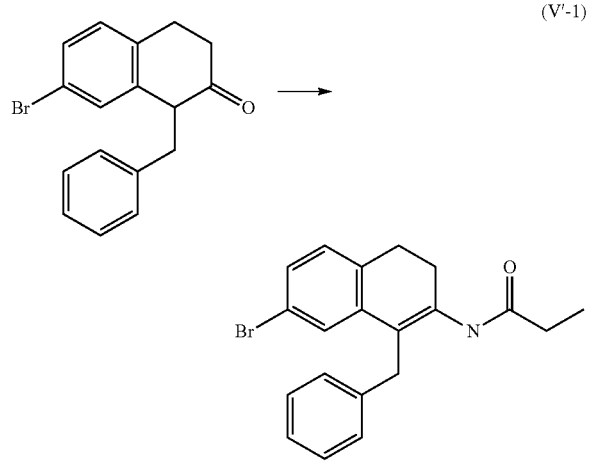

In a three-necked flask equipped with a Dean-Stark apparatus, heating mantle and magnetic stirrer were charged 1-benzyl-7-bromo-3,4-dihydronaphthalen-2(1H)-one (23.50 g, 74.6 mmol), propionamide (13.62 g, 186 mmol) and 4-methylbenzenesulfonic acid (1.284 g, 7.46 mmol) followed by toluene (200 ml). The resulting solution was heated to reflux overnight and monitored by HPLC (<6% starting material remained). The reaction mixture was cooled to r.t. and a suspension formed. To the mixture was added IPA and the resulting suspension was cooled to 0° C., stirred at 0° C. for 2 hours and filtered. The filtrate was concentrated and the residue was suspended in IPA/EtOH (50 ml/50 ml) at 0° C. for 1 hr and filtered to give additional product as a white solid. HPLC analysis indicated that both crops have similar purity. The solids were combined and further dried to give 22.5 g product as white solid.

MS data: $C_{20}H_{20}BrNO$, MW 370.3, $[M+NH_4]^+=387$.

$^1$H NMR data: (400 MHz, $CDCL_3$) δ 8.76 (s, 1H), 7.40-7.07 (m, 7H), 6.98 (d, J=7.9 Hz, 1H), 3.86 (s, 2H), 2.90-2.60 (m, 4H), 2.40-2.24 (m, 2H), 1.10 (t, J=7.5 Hz, 3H).

Example 2b

N-(1-benzyl-7-methoxy-3,4-dihydronaphthalen-2-yl)propionamide

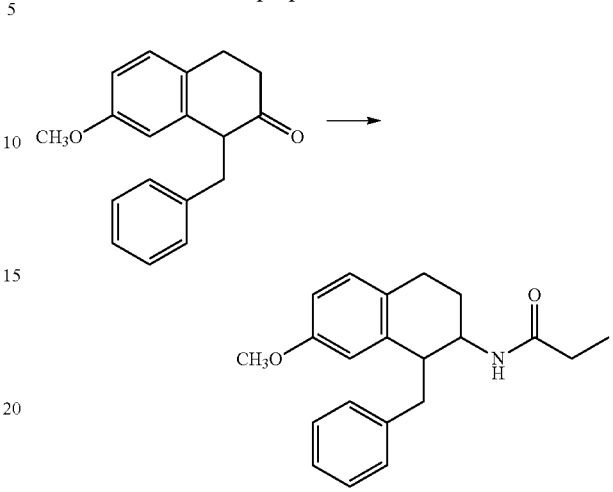

In a three-necked flask equipped with a Dean-Stark apparatus, heating mantle and magnetic stirrer were charged 1-benzyl-7-methoxy-3,4-dihydronaphthalen-2(1H)-one (120 g, 451 mmol), propionamide (82 g, 1126 mmol) and p-toluenesulfonic acid monohydrate (17.14 g, 90 mmol) followed by toluene (1.8 l). The resulting solution was heated to reflux for 5 days and monitored by HPLC (about 16% of starting material remained). The reaction mixture was cooled to r.t. and washed with 8% aqueous sodium bicarbonate solution (250 ml) and water (250 ml). The layers were separated. The organic layer was concentrated to near dryness and chase distilled with IPA (100 ml). The crude product was transferred to a flask equipped with a mechanical stirrer, heating mantle and nitrogen inlet. IPA (500 ml) was added to the flask and suspension was heated to 62° C. and all the solids were dissolved. The suspension was allowed to cool over 2 hrs to 30° C. then cooled to 5° C. Solids were filtered and washed with mixture of heptane/IPA (4:1, 100 ml). Solids were dried under vacuum to give 93.5 g (yield: 65%) product as a white solid.

MS data: $C_{21}H_{23}NO_2$, MW 321.4, $[M+NH_4]^+=338$.

$^1$H NMR data: (400 MHz, $CDCL_3$) 7.34-7.04 (m, 6H), 6.60-6.65 (m, 3H), 3.84 (s, 2H), 3.65 (s, 3H), 2.90-2.65 (m, 4H), 2.22-2.18 (m, 2H), 1.10 (t, J=7.5 Hz, 3H).

III. Preparation of Bicyclic Amine Derivatives of the Formula (Ia)

Example 3a

N-((1R,2S)-1-benzyl-7-methoxy-1,2,3,4-tetrahydronaphthalen-2-yl)propionamide

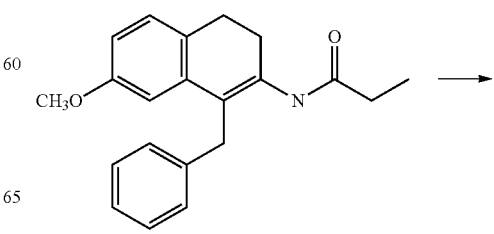

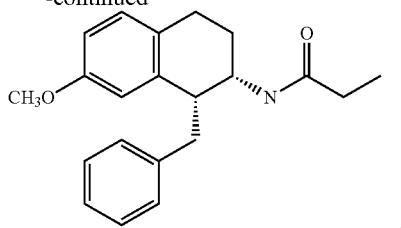

Chlorocyclooctadiene rhodium(I) dimer (0.802 g, 1.63 mmol, 3.25 mmol of Rh), Josiphos SL-J216-2 (2.199 g, 3.42 mmol), and N-(1-benzyl-7-methoxy-3,4-dihydronaphthalen-2-yl)propionamide (440 g, 1.37 mol) were combined in a metal reactor, and the vessel was inerted with argon. Degassed methanol (4.40 l) was added, then the mixture was stirred under argon at 50° C. for 20 min. The vessel was pressurized with 60 psig of hydrogen and stirred at 55° C. for 40 hrs. HPLC analysis indicated complete conversion and 95.9% ee. The methanol solution of crude reduction product was concentrated and triturated with heptane to yield 428.2 g (yield: 91%) of the title compound.

Alternatively, the methanol solution of crude product was concentrated to remove most of the methanol. To the resulting gummy solid was added heptane (7-8 vol). The mixture was heated to reflux and the resulting solution (biphasic) was clarified through a 0.45 micron filter. The resulting solution was concentrated to remove more of the methanol followed by chasing the solids with an additional heptane (7-8 vol). After the heptane chase, heptane (7-8 vol) was added and the slurry was heated to reflux. The slurry was then cooled to RT and filtered. The solid was washed with heptane (5 vol) and then dried in the vacuum oven at 40° C. to yield 428.2 g of dry product (99.6% ee; yield 91%).

MS data: $C_{21}H_{25}NO_2$, MW 323.4, $[M+H]^+=324$.

$^1$H-NMR data: 7.27 (2H, m), 7.20 (1H, m), 7.12 (2H, m), 7.00 (1H, d), 6.70 (1H, d), 6.36 (1H, d), 5.32 (NH, d), 4.31 (1H, m), 3.59 (3H, s), 3.38 (1H, m), 2.90 (4H, m), 2.01 (3H, m), 1.86 (1H, m), 1.06, (3H, t).

Example 3b

N-((1R,2S)-1-benzyl-7-methoxy-1,2,3,4-tetrahydronaphthalen-2-yl)propionamide

The procedure of Example 3a was repeated with the only variation that chloronorbornadiene rhodium(I) dimer was used instead of chlorocyclooctadiene rhodium(I) dimer. The reaction resulted in the same product having almost identical yields and % ee.

Example 4

N-((1R,2S)-1-(3-chlorobenzyl)-7-methoxy-1,2,3,4-tetrahydronaphthalen-2-yl)propionamide

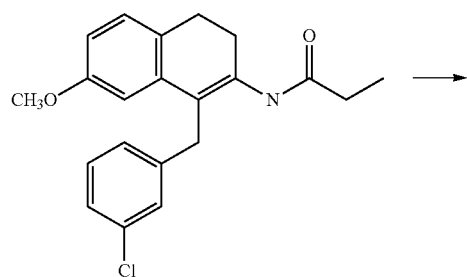

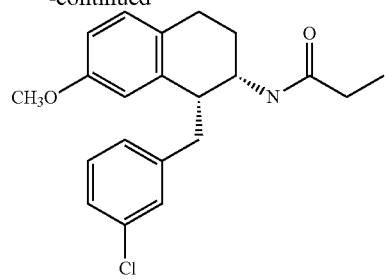

Chlorocyclooctadiene rhodium(I) dimer (29.2 mg, 0.118 mmol of Rh), Josiphos SL-J216-2 (79.1 mg, 0.123 mmol), and N-(1-(3-chlorobenzyl)-7-methoxy-3,4-dihydronaphthalen-2-yl)propionamide (43.30 g, 122 mmol) were combined in a metal reactor, and the vessel was inerted with argon. Degassed methanol (435 ml) was added, then the mixture was agitated under argon at 45° C. for 20 min. The reactor was pressurized to 60 psig with hydrogen and agitated at 60° C. for 16 hrs. HPLC analysis showed complete conversion and 95.2% ee. The mixture was concentrated, and the resulting solid was slurried in heptane and dried in vacuo at 40° C. to yield 42.8 g (yield: 95%) of the title compound.

MS data: $C_{21}H_{24}ClNO_2$, MW 357.9, $[M+H]^+=358/360$ (3:1).

$^1$NMR data: 7.18 (2H, m), 7.09 (1H, bs), 6.99 (2H, m), 6.70 (1H, dd), 6.29 (1H, d), 5.41 (NH, d), 4.29 (1H, m), 3.60 (3H, s), 3.35 (1H, m), 2.85 (4H, m), 2.08 (2H, m) 1.95 (1H, m), 1.86 (1H, m), 1.11 (3H, t).

Example 5

N-((1R,2S)-1-(3-fluorobenzyl)-7-methoxy-1,2,3,4-tetrahydronaphthalen-2-yl)propionamide

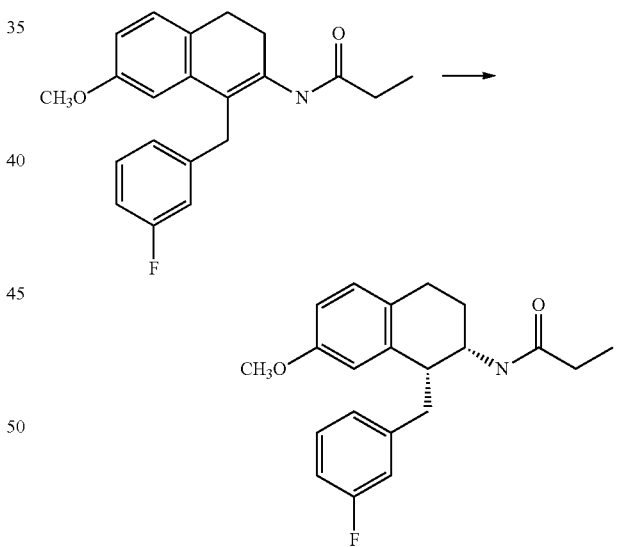

Chlorocyclooctadiene rhodium(I) dimer (0.165 g, 0.669 mmol of Rh), Josiphos SL-J216-2 (0.451 g, 0.702 mmol), and N-(1-(3-fluorobenzyl)-7-methoxy-3,4-dihydronaphthalen-2-yl)propionamide (45.4 g, 134 mmol) were combined in a metal reactor, and the vessel was inerted with argon. Degassed methanol (223 ml) was added, and the reactor was agitated under argon for 20 min at 50° C. The reactor was pressurized with 60 psig of hydrogen and stirred at 60° C. for 30 hrs. HPLC analysis indicated complete conversion and 95.2% ee. The mixture was concentrated, filtered in EtOAc through silica gel, concentrated, slurried in hot heptane, filtered, and dried to yield 39.6 g (yield: 87%) of the title compound.

MS data: $C_{21}H_{24}FNO_2$, MW 341.4, $[M+H]^+=342$.

$^1$NMR data: 7.22 (1H, m), 7.01 (1H, d), 6.90 (2H, m), 6.83 (1H, dt), 6.71 (1H, dd), 6.34 (1H, d), 5.29 (NH, d), 4.30 (1H, m), 3.61 (3H, s), 3.38 (1H, m), 2.88 (4H, m), 2.08 (2H, m) 1.96 (1H, m), 1.86 (1H, m), 1.10 (3H, t).

Example 6

N-((1R,2S)-1-benzyl-7-bromo-1,2,3,4-tetrahydronaphthalen-2-yl)propionamide

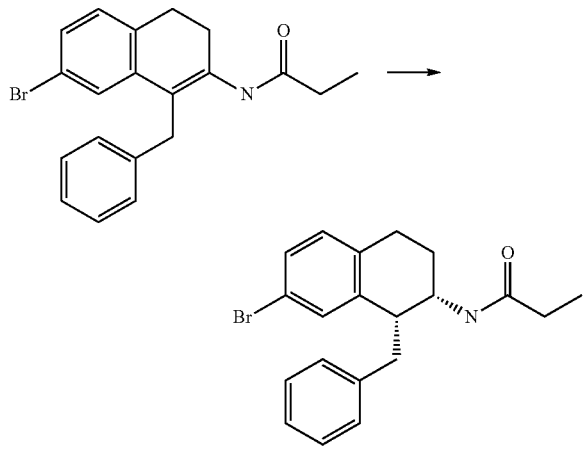

Chlorocyclooctadiene rhodium(I) dimer (0.217 g, 0.881 mmol of Rh), Josiphos SL-J216-2 (0.595 g, 0.926 mmol), and N-(1-benzyl-7-bromo-3,4-dihydronaphthalen-2-yl)propionamide (10.88 g, 29.4 mmol) were combined in a metal reactor, and the vessel was inerted with argon. Degassed ethanol (163 ml) was added, and the mixture was agitated under argon for 30 min at 50° C. The vessel was pressurized with 60 psig of hydrogen and agitated at 55° C. for 14.5 hrs. HPLC analysis indicated 89.4% conversion and 93.8% ee. The mixture was concentrated, and the resulting solid was crystallized from MeOH to yield 7.41 g (yield: 68%) of the title compound.

MS data: $C_{20}H_{22}BrNO$, MW 372.3, $[M+H]^+=372/374$ (1:1).

$^1$NMR data: 7.30 (2H, m), 7.23 (2H, m), 7.13 (1H, d), 7.11 (1H, m), 7.01 (1H, d), 6.97, (1H, d), 5.23 (NH, d), 4.28 (1H, m), 3.36 (1H, dt), 2.87 (4H, m), 1.97 (3H, m) 1.86 (1H, m), 1.04 (3H, t).

Example 7

N-((1R,2S)-1-benzyl-6-fluoro-7-methoxy-1,2,3,4-tetrahydronaphthalen-2-yl)propionamide

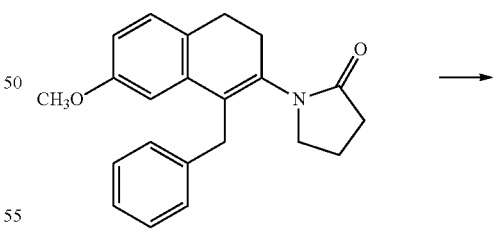

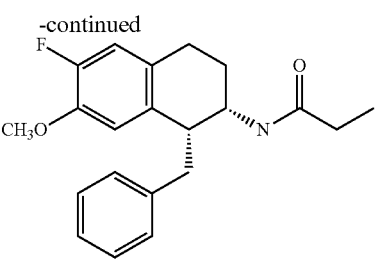

Chlorocyclooctadiene rhodium(I) dimer (0.648 g, 2.63 mmol of Rh), Josiphos SL-J216-2 (1.779 g, 2.77 mmol), and N-(1-benzyl-6-fluoro-7-methoxy-3,4-dihydronaphthalen-2-yl)propionamide (93.96 g, 277 mmol) were combined in a metal reactor, and the vessel was inerted with argon. Degassed methanol (940 ml) was added, and the mixture was agitated under 20 psi of argon at 50° C. for 20 min. The vessel was pressurized with 60 psig of hydrogen and agitated at 55° C. for 14 hrs. HPLC analysis indicated complete conversion and 94.7% ee. The mixture was concentrated, and the resulting solid was precipitated from MeOH to yield 86.9 g (yield: 92%) of the title compound.

Alternatively, the methanol solution of crude product was concentrated to remove most of the methanol. To the resulting gummy solid was added heptane (7-8 vol). The mixture was heated to reflux and the resulting solution (biphasic) was clarified through a 0.45 micron filter. The resulting solution was concentrated to remove more of the methanol followed by chasing the solids with an additional heptane (7-8 vol). After the heptane chase, heptane (7-8 vol) was added and the slurry was heated to reflux. The slurry was then cooled to RT and filtered. The solid was washed with heptane (5 vol) and then dried in the vacuum oven at 40° C. to yield 86.9 g of dry product (94.7% ee; yield 92%).

MS data: $C_{21}H_{24}FNO_2$, MW 341.4, $[M+H]^+=342$.

$^1$NMR data: 7.32 (2H, t), 7.23 (1H, t), 7.11 (2H, d), 6.82 (1H, d), 6.14 (1H, d), 5.44 (NH, d), 4.35 (1H, m), 3.56 (3H, s), 3.41 (1H, m), 3.01 (1H, dd), 2.91 (2H, m), 2.71 (1H, dd), 2.15 (2H, m), 2.02 (1H, m), 1.90 (1H, m), 1.16 (3H, t).

Example 8

N-((1R,2S)-1-benzyl-7-methoxy-1,2,3,4-tetrahydronaphthalen-2-yl)pyrrolidin-2-one

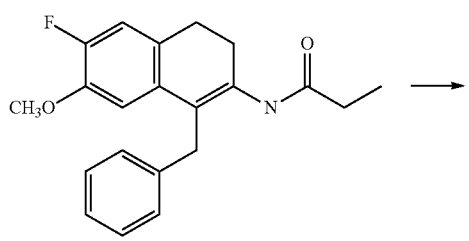

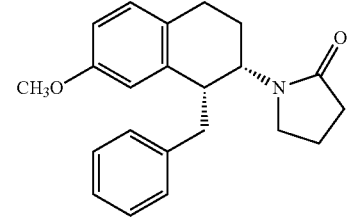

Chlorocyclooctadiene rhodium(I) dimer (3.70 mg, 15.0 µmol of Rh), Josiphos SL-J216-2 (10.16 mg, 16.0 µmol), and N-(1-benzyl-7-methoxy-3,4-dihydronaphthalen-2-yl)pyrrolidin-2-one (500.8 mg, 1.50 mmol) were combined in a glass-lined metal reactor, and the vessel was inerted with argon. Degassed methanol (5.0 ml) was added, and the mixture was agitated under 20 psi of argon at 50° C. for 20 min. The vessel was pressurized with 90 psig of hydrogen and stirred at 100° C. for 45 hrs. HPLC analysis indicated 99.8% conversion and 90.7% ee. The mixture was concentrated and diluted with water to yield 415 mg (yield: 82%) of the title compound.

MS data: $C_{21}H_{24}FNO_2$, MW 335.44, $[M+H]^+$=336, $[M+NH_4]^+$=353.

$^1$NMR data: 7.29 (2H, t), 7.21 (1H, t), 7.14 (2H, d), 7.01 (1H, d), 6.69 (1H, dd), 6.07 (1H, d), 4.45 (1H, dt), 3.63 (1H, dt), 3.50 (3H, s), 3.44 (1H, t), 3.38 (1H, td), 3.01 (1H, dd), 2.95 (1H, dd), 2.90, 1H, dd), 2.81 (1H, dd), 2.35 (2H, dt), 2.17 (1H, m), 2.08 (1H, m), 1.93 (1H, m), 1.79 (1H, m), 1.64 (1H, bs).

IV. Preparation of Bicyclic Amine Derivatives of the Formula (Ib)

Example 9

N-((1S,2R)-1-benzyl-7-methoxy-1,2,3,4-tetrahydronaphthalen-2-yl)propionamide

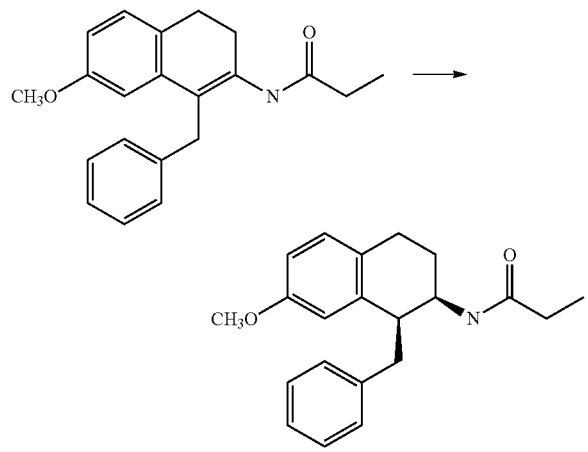

Chlorocyclooctadiene rhodium(I) dimer (0.072 g, 0.292 mmol), Josiphos SL-J216-1 (0.197 g, 0.307 mmol), and N-(1-benzyl-7-methoxy-3,4-dihydronaphthalen-2-yl)propionamide (19.75 g, 61.4 mmol) were combined in a 500 ml SS pressure bottle, and the vessel was inerted with argon. Degassed methanol (200 ml) was added, the vessel was again inerted, then the mixture was stirred under 20 psig of argon at 50° C. for 20 min. The vessel was then pressurized with 60 psig of hydrogen and stirred at 55° C. for 14 hrs. HPLC analysis (YIYINADH.M, s.m. 9.08 min. with a 1.5 PA % impurity at 12.14 min., product enantiomers 9.45 and 13.41 min.) indicated 100% conversion and 95.6% ee. Crystallization from MeOH afforded the title compound (yield: 15%; ee: 99.5%).

We claim:

1. A process for preparing a bicyclic amine derivative of the formula (Ia) or (Ib),

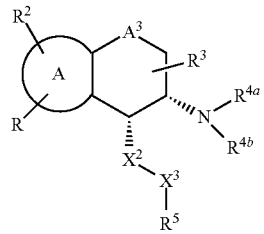

(Ia)

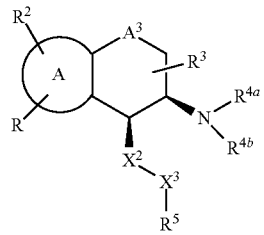

(Ib)

wherein
A is a benzene ring;
R is hydrogen, halogen, —CN, hydroxyl which optionally carries a protecting group, a group $Y'\text{-}A^2\text{-}X^1$—, or a group $R^1\text{—W-A}^1\text{-Q-Y-A}^2\text{-}X^1$—;
$R^1$, is hydrogen, $C_1\text{-}C_6$-alkyl, $C_3\text{-}C_{12}$-cycloalkyl-$C_1\text{-}C_4$-alkyl, halogenated $C_1\text{-}C_6$-alkyl, tri-($C_1\text{-}C_4$-alkyl)-silyl-$C_1\text{-}C_4$-alkyl, hydroxy-$C_1\text{-}C_4$-alkyl, $C_1\text{-}C_6$-alkoxy-$C_1\text{-}C_4$-alkyl, amino-$C_1\text{-}C_4$-alkyl, $C_1\text{-}C_6$-alkylamino-$C_1\text{-}C_4$-alkyl, di-$C_1\text{-}C_6$-alkylamino-$C_1\text{-}C_4$-alkyl, $C_1\text{-}C_6$-alkylcarbonylamino-$C_1\text{-}C_4$-alkyl, $C_1\text{-}C_6$-alkyloxycarbonylamino-$C_1\text{-}C_4$-alkyl, $C_1\text{-}C_6$-alkylaminocarbonylamino-$C_1\text{-}C_4$-alkyl, di-$C_1\text{-}C_6$-alkylaminocarbonylamino-$C_1\text{-}C_4$-alkyl, $C_1\text{-}C_6$-alkylsulfonylamino-$C_1\text{-}C_4$-alkyl, (optionally substituted $C_6\text{-}C_{12}$-aryl-$C_1\text{-}C_6$-alkyl)amino-$C_1\text{-}C_4$-alkyl, optionally substituted $C_6\text{-}C_{12}$-aryl-$C_1\text{-}C_4$-alkyl, optionally substituted $C_3\text{-}C_{12}$-heterocyclyl-$C_1\text{-}C_4$-alkyl, $C_3\text{-}C_{12}$-cycloalkyl, $C_1\text{-}C_6$-alkylcarbonyl, $C_1\text{-}C_6$-alkoxycarbonyl, halogenated $C_1\text{-}C_6$-alkoxycarbonyl, $C_6\text{-}C_{12}$-aryloxycarbonyl, aminocarbonyl, $C_1\text{-}C_6$-alkylaminocarbonyl, (halogenated $C_1\text{-}C_4$-alkyl)aminocarbonyl, $C_6\text{-}C_{12}$-arylaminocarbonyl, $C_2\text{-}C_6$-alkenyl, $C_2\text{-}C_6$-alkynyl, optionally substituted $C_6\text{-}C_{12}$-aryl, hydroxy, $C_1\text{-}C_6$-alkoxy, halogenated $C_1\text{-}C_6$-alkoxy, $C_1\text{-}C_6$-hydroxyalkoxy, $C_1\text{-}C_6$-alkoxy-$C_1\text{-}C_4$-alkoxy, amino-$C_1\text{-}C_4$-alkoxy, $C_1\text{-}C_6$-alkylamino-$C_1\text{-}C_4$-alkoxy, di-$C_1\text{-}C_6$-alkylamino-$C_1\text{-}C_4$-alkoxy, $C_1\text{-}C_6$-alkylcarbonylamino-$C_1\text{-}C_4$-alkoxy, $C_6\text{-}C_{12}$-arylcarbonylamino-$C_1\text{-}C_4$-alkoxy, $C_1\text{-}C_6$-alkoxycarbonylamino-$C_1\text{-}C_4$-alkoxy, $C_6\text{-}C_{12}$-aryl-$C_1\text{-}C_4$-alkoxy, $C_1\text{-}C_6$-alkylsulfonylamino-$C_1\text{-}C_4$-alkoxy, (halogenated $C_1\text{-}C_6$-alkyl)sulfonylamino-$C_1\text{-}C_4$-alkoxy, $C_6\text{-}C_{12}$-arylsulfonylamino-$C_1\text{-}C_4$-alkoxy, ($C_6\text{-}C_{12}$-aryl-$C_1\text{-}C_6$-alkyl)sulfonylamino-$C_1\text{-}C_4$-alkoxy, $C_3\text{-}C_{12}$-heterocyclylsulfonylamino-$C_1\text{-}C_4$-alkoxy, $C_3\text{-}C_{12}$-heterocyclyl-$C_1\text{-}C_4$-alkoxy, $C_6\text{-}C_{12}$-aryloxy, $C_3\text{-}C_{12}$-heterocyclyloxy, $C_1\text{-}C_6$-alkylthio, halogenated $C_1\text{-}C_6$-alkylthio, $C_1\text{-}C_6$-alkylamino, (halogenated $C_1\text{-}C_6$-alkyl)amino, di-$C_1\text{-}C_6$-alkylamino, di-(halogenated $C_1\text{-}C_6$-alkyl)amino, $C_1\text{-}C_6$-alkylcarbonylamino, (halogenated $C_1\text{-}C_6$-alkyl)carbonylamino, $C_6\text{-}C_{12}$-arylcarbonylamino, $C_1\text{-}C_6$-alkylsulfonylamino, (halogenated $C_1\text{-}C_6$-alkyl)sulfonylamino, $C_6\text{-}C_{12}$-arylsulfonylamino or optionally substituted $C_3\text{-}C_{12}$-heterocyclyl;

W is —NR$^8$— or a bond;
A$^1$ is optionally substituted C$_1$-C$_4$-alkylene or a bond;
Q is —S(O)$_2$— or —C(O)—;
Y is —NR$^9$— or a bond;
Y' is Y which optionally carries a protecting group;
A$^2$ is optionally substituted C$_1$-C$_4$-alkylene, C$_1$-C$_4$-alkylene-CO—, —CO—C$_1$-C$_4$-alkylene, C$_1$-C$_4$-alkylene-O—C$_1$-C$_4$-alkylene, C$_1$-C$_4$-alkylene-NR$^{10}$—C$_1$-C$_4$-alkylene, optionally substituted C$_2$-C$_4$-alkenylene, optionally substituted C$_2$-C$_4$-alkynylene, optionally substituted C$_6$-C$_{12}$-arylene, optionally substituted C$_6$-C$_{12}$-heteroarylene or a bond;
X$^1$ is —O—, —NR$^{11}$—, —S—, optionally substituted C$_1$-C$_4$-alkylene, optionally substituted C$_2$-C$_4$-alkenylene, or optionally substituted C$_2$-C$_4$-alkynylene;
R$^2$ is hydrogen, halogen, C$_1$-C$_6$-alkyl, halogenated C$_1$-C$_4$-alkyl, hydroxy-C$_1$-C$_4$-alkyl, —CN, C$_2$-C$_6$-alkenyl, C$_2$-C$_6$-alkynyl, optionally substituted C$_6$-C$_{12}$-aryl, hydroxy, C$_1$-C$_6$-alkoxy, halogenated C$_1$-C$_6$-alkoxy, C$_1$-C$_6$-alkoxycarbonyl, C$_2$-C$_6$-alkenyloxy, C$_6$-C$_{12}$-aryl-C$_1$-C$_4$-alkoxy, C$_1$-C$_6$-alkylcarbonyloxy, C$_1$-C$_6$-alkylthio, C$_1$-C$_6$-alkylsulfinyl, C$_1$-C$_6$-alkylsulfonyl, aminosulfonyl, amino, C$_1$-C$_6$-alkylamino, C$_2$-C$_6$-alkenylamino, nitro or optionally substituted C$_3$-C$_{12}$-heterocyclyl, or two radicals R$^2$ together with the ring atoms of A to which they are bound form a 5- or 6-membered ring;
A$^3$ is —CH$_2$—;
R$^3$ is hydrogen;
R$^{4a}$ is C$_1$-C$_4$-alkylcarbonyl, (halogenated C$_1$-C$_4$-alkyl)carbonyl or C$_6$-C$_{12}$-arylcarbonyl;
R$^{4b}$ is hydrogen or C$_1$-C$_6$-alkyl; or
R$^{4a}$, R$^{4b}$
together are C$_2$-C$_{10}$-alkylenecarbonyl;
X$^2$ is —CH$_2$—;
X$^3$ is a bond;
R$^5$ is optionally substituted C$_6$-C$_{12}$-aryl;
R$^8$ is hydrogen or C$_1$-C$_6$-alkyl;
R$^9$ is hydrogen, C$_1$-C$_6$-alkyl, C$_3$-C$_{12}$-cycloalkyl, amino-C$_1$-C$_6$-alkyl, optionally substituted C$_6$-C$_{12}$-aryl-C$_1$-C$_4$-alkyl or C$_3$-C$_{12}$-heterocyclyl; or
R$^9$, R$^1$
together are C$_1$-C$_4$-alkylene; or
R$^9$ is C$_1$-C$_4$-alkylene that is bound to a carbon atom in A$^2$ and A$^2$ is C$_1$-C$_4$-alkylene or to a carbon atom in X$^1$ and X$^1$ is C$_1$-C$_4$-alkylene;
R$^{10}$ is hydrogen, C$_1$-C$_6$-alkyl or C$_1$-C$_6$-alkylsulfonyl; and
R$^{11}$ is hydrogen or C$_1$-C$_6$-alkyl, or
R$^9$, R$^{11}$
together are C$_1$-C$_4$-alkylene;
or a salt thereof;
comprising the rhodium-catalyzed asymmetric hydrogenation of an enamine of the formula (II),

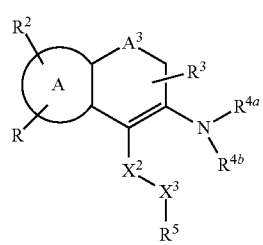

(II)

wherein A, A$^3$, R, R$^2$, R$^3$, R$^{4a}$, R$^{4b}$, R$^5$, X$^2$ and X$^3$ are as defined above,
or of a salt thereof;
in the presence of a chiral diphoshine ligand;
wherein the rhodium catalyst is a rhodium(I) compound of formula (IIIa), (IIIb) or (IIIC),

[Rh Li$^1$ An]$_2$ (IIIa)

[Rh Li$^2$$_2$ An]$_n$ (IIIb)

[Rh Li$^1$$_2$ An] (IIIc)

wherein
Li$^1$ is C$_5$-C$_{12}$-alkadiene, C$_5$-C$_{12}$-cycloalkadiene or C$_5$-C$_{12}$-bicycloalkadiene;
Li$^2$ is C$_2$-C$_{12}$-alkene or C$_5$-C$_8$-cycloalkene;
n is 1 or 2; and
An is halide, tetrafluoroborate, trifluoromethanesulfonate or acetylacetonate;
and
wherein the diphosphine ligand is of the formula (Iva), (IVb), (IVc) or (IVd),

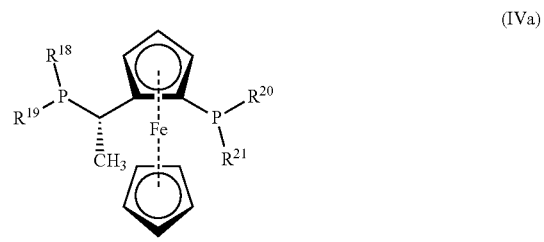

(IVa)

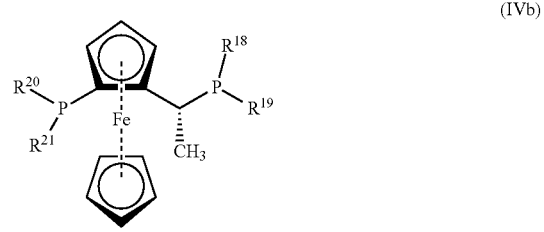

(IVb)

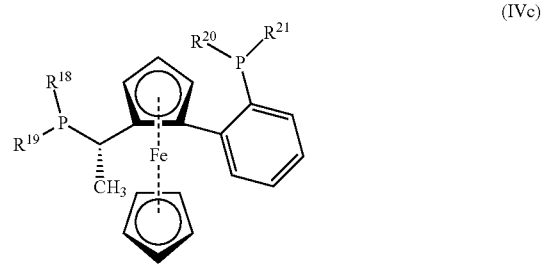

(IVc)

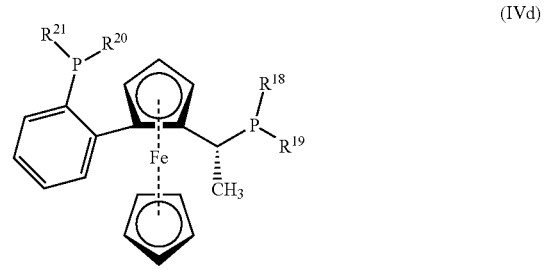

(IVd)

wherein

R$^{18}$, R$^{19}$, R$^{20}$ and R$^{21}$, independently of each other, are selected from the group consisting of C$_1$-C$_{12}$-alkyl, C$_5$-C$_7$-cycloalkyl, C$_3$-C$_6$-hetaryl and C$_6$-C$_{12}$aryl, wherein C$_3$-C$_6$-hetaryl and C$_6$-C$_{12}$-aryl are unsubstituted or carry 1, 2, 3, 4, or 5 substituents selected from the group consisting of C$_1$-C$_4$-alkyl, C$_1$-C$_4$-alkoxy and di-C$_1$-C$_4$-alkylamine.

2. The process as claimed in claim 1, wherein the rhodium (I) compound is of formula (IIIa) with Li$^1$ being C$_6$-C$_{10}$-cycloalkadiene or C$_5$-C$_{12}$-bicycloalkadiene, and An being chloride.

3. The process as claimed in claim 1, wherein the diphosphine ligand is of the formula (IVa) or (IVb) with R$^{18}$ and R$^{19}$ having the same meaning and R$^{20}$ and R$^{21}$ having the same meaning.

4. The process as claimed in claim 3, wherein R$^{18}$ and R$^{19}$ are both C$_1$-C$_{12}$-alkyl and R$^{20}$ and R$^{21}$ are both optionally substituted C$_3$-C$_5$-hetaryl or optionally substituted C$_6$-C$_{10}$-aryl.

5. The process as claimed in claim 4, wherein R$^{18}$ and R$^{19}$ are both tert-butyl and R$^{20}$ and R$^{21}$ are both 1-naphthyl or 2-furyl.

6. The process as claimed in claim 1, which further comprises:

(a) providing a ketone of the formula (V),

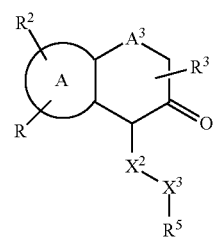

(V)

and (b) converting the ketone of the formula (V) into the enamine of the formula (II).

7. The process as claimed in claim 1, wherein the bicyclic amine derivative is a compound of the formula (Ia) and the chiral diphosphine ligand is the diphosphine of formula (IVa).

8. The process as claimed in claim 1, wherein, in formulae (Ia), (Ib) and (II), R$^{4a}$ is C$_1$-C$_4$-alkylcarbonyl or (halogenated C$_1$-C$_4$-alkyl)carbonyl and R$^{4b}$ is hydrogen or C$_1$-C$_6$-alkyl; or R$^{4a}$, R$^{4b}$ together are C$_2$-C$_6$-alkylenecarbonyl.

9. The process as claimed in claim 1, further comprising crystallizing from heptane, methanol or a mixture of heptane and methanol the compound of formula (Ia) or (Ib), wherein R is —OCH$_3$, R$^2$ is hydrogen, R$^{4a}$ is ethoxycarbonyl, R$^{4b}$ is hydrogen, and R$^5$ is phenyl.

* * * * *